United States Patent
Liu et al.

(10) Patent No.: US 12,049,492 B2
(45) Date of Patent: Jul. 30, 2024

(54) CR3022 CHIMERIC ANTIGEN RECEPTORS AND METHODS OF USE

(71) Applicant: Rutgers, The State University of New Jersey, New Brunswick, NJ (US)

(72) Inventors: Dongfang Liu, Millburn, NJ (US);
Minh Ma, New Brunswick, NJ (US);
Saiaditya Badeti, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 207 days.

(21) Appl. No.: 17/399,993

(22) Filed: Aug. 11, 2021

(65) Prior Publication Data
US 2022/0048978 A1     Feb. 17, 2022

Related U.S. Application Data

(60) Provisional application No. 63/064,156, filed on Aug. 11, 2020.

(51) Int. Cl.
*C07K 16/10*     (2006.01)
*A61K 35/15*     (2015.01)
(Continued)

(52) U.S. Cl.
CPC ............... *C07K 16/10* (2013.01); *A61K 35/15* (2013.01); *A61K 35/17* (2013.01); *A61P 31/14* (2018.01);
(Continued)

(58) Field of Classification Search
CPC ................. C07K 16/10; C07K 14/7051; C07K 14/70521; C07K 14/7151; C07K 2317/24; C07K 2317/53; C07K 2317/56; C07K 2317/565; C07K 2319/03; C07K 2319/33; C07K 2317/622; C07K 2317/73; A61K 35/15; A61K 35/17; A61K 39/00;
(Continued)

(56) References Cited

U.S. PATENT DOCUMENTS 11,021,532 B1     6/2021  Glanville et al.
2022/0033460 A1*  2/2022  Pregibon ................ A61K 39/12

FOREIGN PATENT DOCUMENTS

WO    WO-2021205183 A1 * 10/2021
WO    WO-2022029011 A1 *  2/2022

OTHER PUBLICATIONS

"MARKET" Market M, Angka L, Martel AB, Bastin D, Olanubi O, Tennakoon G, Boucher DM, Ng J, Ardolino M, Auer RC. Flattening the COVID-19 Curve With Natural Killer Cell Based Immunotherapies. Front Immunol. Jun. 23, 2020;11:1512 (Year: 2020).*

(Continued)

*Primary Examiner* — Jeremy C Flinders
*Assistant Examiner* — Thomas R. Amick
(74) *Attorney, Agent, or Firm* — Klarquist Sparkman, LLP

(57) ABSTRACT

Chimeric antigen receptors (CARs) including an antigen binding domain specifically binding to coronavirus spike protein, nucleic acids encoding the CARs, vectors including nucleic acids encoding the CARs, and immune cells expressing the CARs are provided. Methods of treating a subject with coronavirus, including administering to the subject an immune cell expressing a disclosed CAR are also provided.

19 Claims, 5 Drawing Sheets

Specification includes a Sequence Listing.

(51) Int. Cl.
*A61K 35/17* (2015.01)
*A61K 39/00* (2006.01)
*A61P 31/14* (2006.01)
*C07K 14/705* (2006.01)
*C07K 14/715* (2006.01)
*C07K 14/725* (2006.01)
*C12N 9/64* (2006.01)

(52) U.S. Cl.
CPC .... *C07K 14/7051* (2013.01); *C07K 14/70521* (2013.01); *C07K 14/7151* (2013.01); *C12N 9/6472* (2013.01); *C12Y 304/22062* (2013.01); *A61K 39/00* (2013.01); *C07K 2317/24* (2013.01); *C07K 2317/53* (2013.01); *C07K 2317/56* (2013.01); *C07K 2317/565* (2013.01); *C07K 2319/03* (2013.01); *C07K 2319/33* (2013.01)

(58) Field of Classification Search
CPC . A61K 39/12; A61K 2039/5156; A61P 31/14; C12N 9/6472; C12Y 304/22062
See application file for complete search history.

(56) References Cited

OTHER PUBLICATIONS

Seif M, Einsele H, Löffler J. Car T Cells Beyond Cancer: Hope for Immunomodulatory Therapy of Infectious Diseases. Front Immunol. Nov. 21, 2019;10:2711 (Year: 2019).*
Gargett T, Brown MP. The inducible caspase-9 suicide gene system as a "safety switch" to limit on-target, off-tumor toxicities of chimeric antigen receptor T cells. Front Pharmacol. Oct. 28, 2014;5:235, (Year: 2014).*
Zhang et al, Front. Immunol. 8:533., May 18, 2017, Sec. Alloimmunity and Transplantation, vol. 8—2017. (Year: 2017).*
Michael Hudecek et al, Cancer Immunol Res Feb. 1, 2015; 3 (2): 125-135 (Year: 2015).*
Ma et al., "Efficacy of Targeting SARS-CoV-2 by CAR-NK Cells," *bioRxiv*, https://doi.org/10.1101/2020.08.11.247320, Aug. 12, 2020 (34 pages).
Tian et al., "Potent binding of 2019 novel coronavirus spike protein by a SARS coronavirus-specific human monoclonal antibody," *Emerging Microbes & Infections*, vol. 9, pp. 382-385, 2020.

* cited by examiner

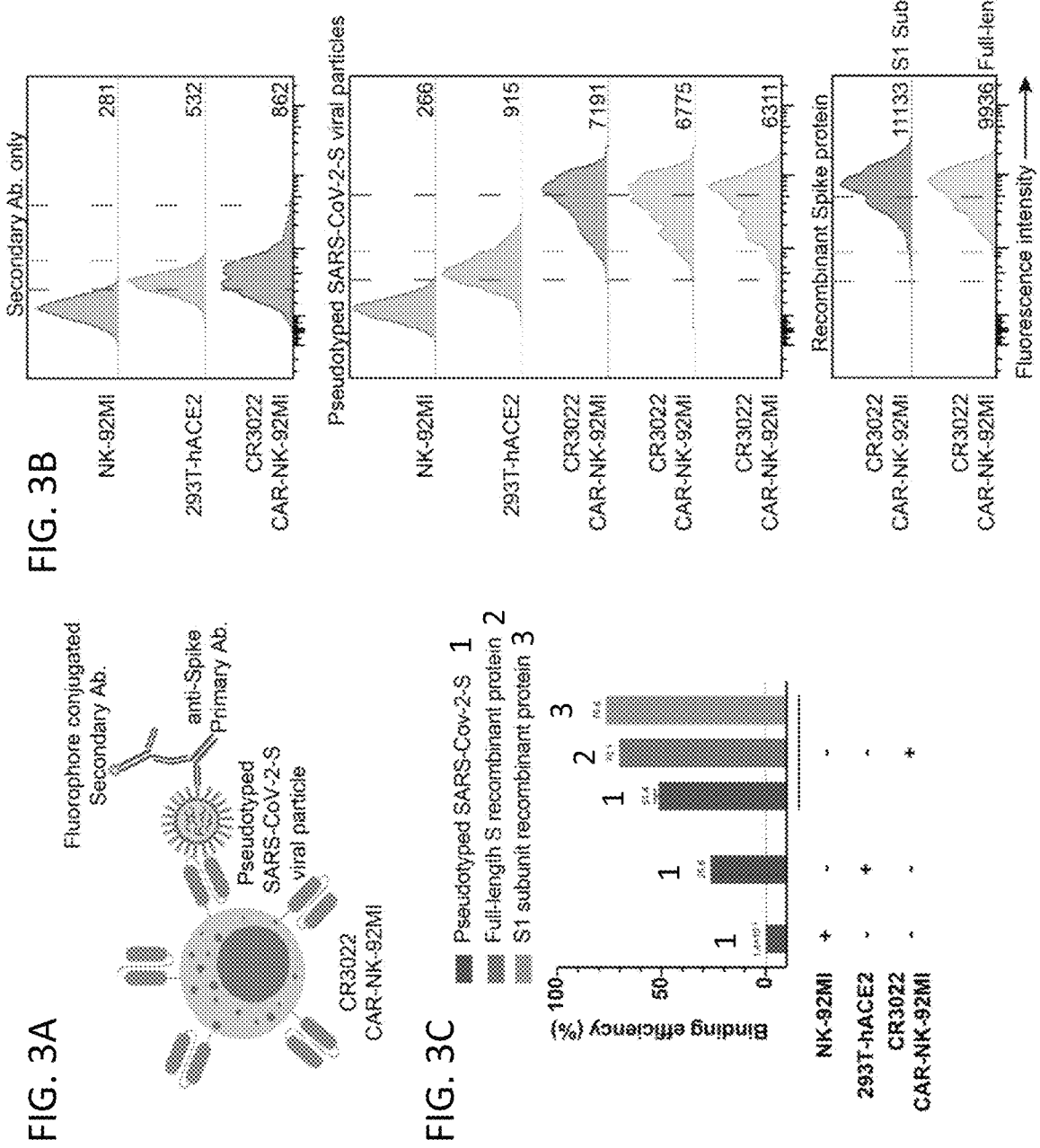

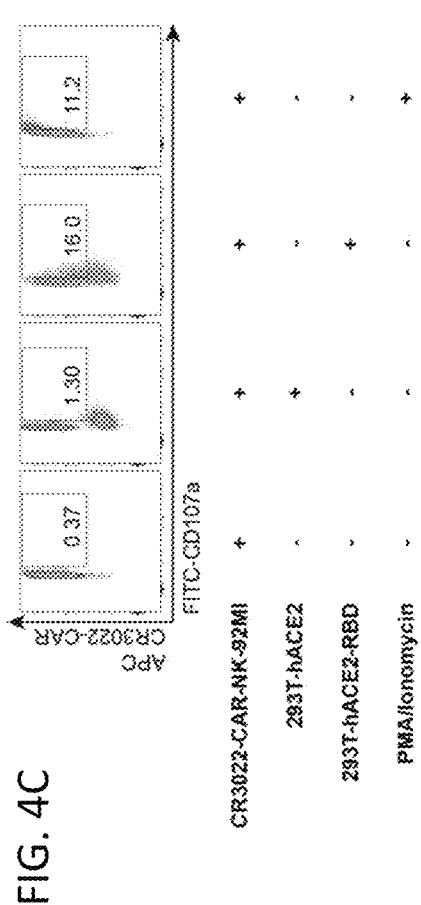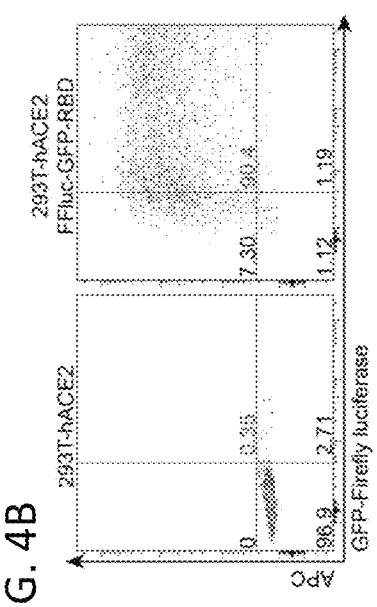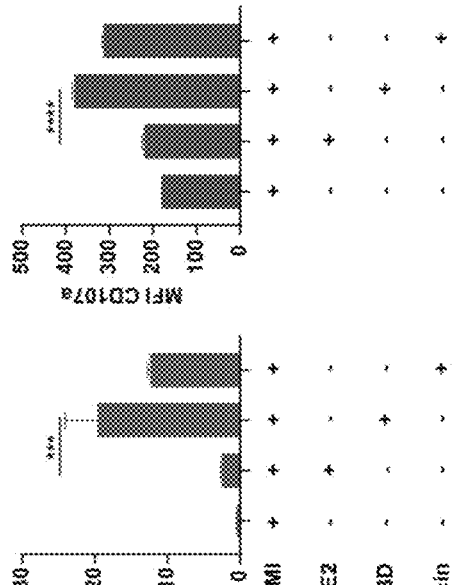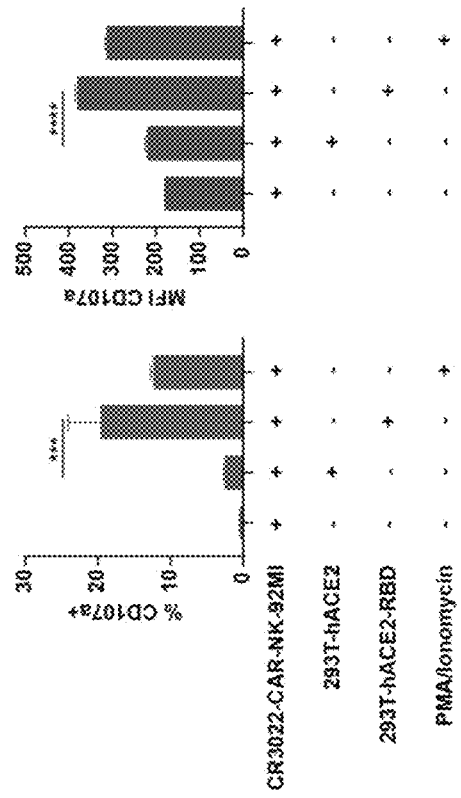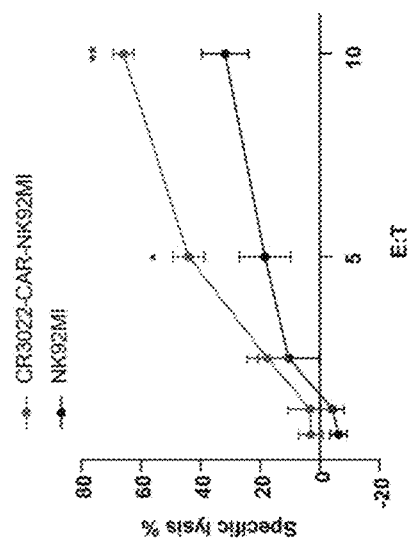
FIG. 4A
FIG. 4B
FIG. 4C
FIG. 4D

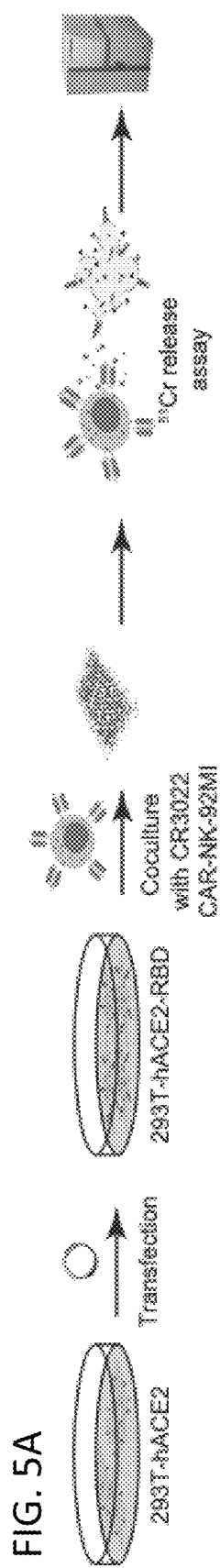
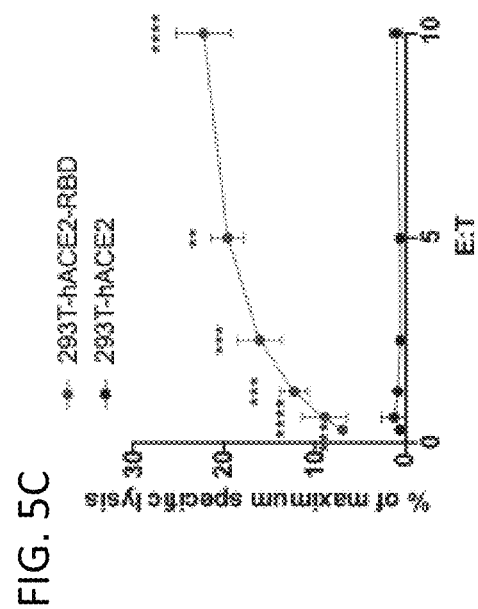
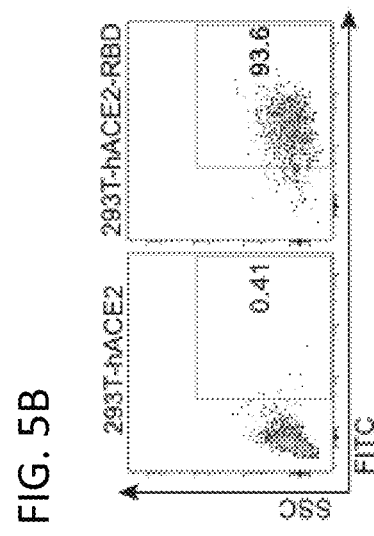
FIG. 5A
FIG. 5B
FIG. 5C

SEQUENCE LISTING

```
<160> NUMBER OF SEQ ID NOS: 8

<210> SEQ ID NO 1
<211> LENGTH: 250
<212> TYPE: PRT
<213> ORGANISM: Artificial Sequence
<220> FEATURE:
<223> OTHER INFORMATION: CR3022 scFv sequence

<400> SEQUENCE: 1

Gln Met Gln Leu Val Gln Ser Gly Thr Glu Val Lys Lys Pro Gly Glu
1               5                   10                  15

Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95
```

```
Ala Gly Gly Ser Gly Ile Ser Thr Pro Met Asp Val Trp Gly Gln Gly
            100                 105                 110

Thr Thr Val Thr Val Gly Gly Gly Ser Gly Gly Gly Gly Ser Gly
        115                 120                 125

Gly Gly Ser Gly Gly Gly Ser Asp Ile Gln Leu Thr Gln Ser
    130                 135                 140

Pro Asp Ser Leu Ala Val Ser Leu Gly Glu Arg Ala Thr Ile Asn Cys
145                 150                 155                 160

Lys Ser Ser Gln Ser Val Leu Tyr Ser Ser Ile Asn Lys Asn Tyr Leu
                165                 170                 175

Ala Trp Tyr Gln Gln Lys Pro Gly Gln Pro Lys Leu Leu Ile Tyr
            180                 185                 190

Trp Ala Ser Thr Arg Glu Ser Gly Val Pro Asp Arg Phe Ser Gly Ser
            195                 200                 205

Gly Ser Gly Thr Asp Phe Thr Leu Thr Ile Ser Ser Leu Gln Ala Glu
        210                 215                 220

Asp Val Ala Val Tyr Tyr Cys Gln Gln Tyr Tyr Ser Thr Pro Tyr Thr
225                 230                 235                 240

Phe Gly Gln Gly Thr Lys Val Glu Ile Lys
                245                 250
```

<210> SEQ ID NO 2
<211> LENGTH: 750
<212> TYPE: DNA
<213> ORGANISM: Artificial Sequence
<220> FEATURE:
<223> OTHER INFORMATION: CR3022 scFv sequence

<400> SEQUENCE: 2

```
cagatgcagc tggtgcaatc tggaacagag gtgaaaaagc cgggggagtc tctgaagatc      60
tcctgtaagg gttctggata cggctttatc acctactgga tcggctgggt gcgccagatg     120
cccgggaaag gcctggagtg gatggggatc atctatcctg gtgactctga accagatac      180
agcccgtcct ccaaggcca ggtcaccatc tcagccgaca gtccatcaa caccgcctac       240
ctgcagtgga gcagcctgaa ggcctcggac accgccatat attactgtgc gggggggttcg    300
gggatttcta cccctatgga cgtctggggc aagggaccca cggtcaccgt cggtggtggt     360
ggttctggtg gtggtggttc tggcggcggc ggctccggtg gtggtggatc cgacatccag     420
ttgacccagt ctccagactc cctggctgtg tctctgggcg agagggccac catcaactgc     480
aagtccagcc agagtgttt atacagctcc atcaataaga actacttagc ttggtaccag     540
cagaaaccag acagcctcc taagctgctc atttactggg catctacccg ggaatccggg     600
gtccctgacc gattcagtgg cagcgggtct gggacagatt tcactctcac catcagcagc     660
ctgcaggctg aagatgtggc agtttattac tgtcagcaat attatagtac tccgtacact     720
tttggccagg ggaccaaggt ggaaatcaaa                                      750
```

<210> SEQ ID NO 3
<211> LENGTH: 740
<212> TYPE: PRT
<213> ORGANISM: Artificial Sequence
<220> FEATURE:
<223> OTHER INFORMATION: CR3022 CAR sequence

<400> SEQUENCE: 3

```
Met Glu Phe Gly Leu Ser Trp Leu Phe Leu Val Ala Ile Leu Lys Gly
1               5                   10                  15
```

```
Val Gln Cys Val Asp Gln Met Gln Leu Val Gln Ser Gly Thr Glu Val
             20                  25                  30

Lys Lys Pro Gly Glu Ser Leu Lys Ile Ser Cys Lys Gly Ser Gly Tyr
         35                  40                  45

Gly Phe Ile Thr Tyr Trp Ile Gly Trp Val Arg Gln Met Pro Gly Lys
 50                  55                  60

Gly Leu Glu Trp Met Gly Ile Ile Tyr Pro Gly Asp Ser Glu Thr Arg
 65                  70                  75                  80

Tyr Ser Pro Ser Phe Gln Gly Gln Val Thr Ile Ser Ala Asp Lys Ser
                 85                  90                  95

Ile Asn Thr Ala Tyr Leu Gln Trp Ser Ser Leu Lys Ala Ser Asp Thr
             100                 105                 110

Ala Ile Tyr Tyr Cys Ala Gly Gly Ser Gly Ile Ser Thr Pro Met Asp
         115                 120                 125

Val Trp Gly Gln Gly Thr Thr Val Thr Val Gly Gly Gly Gly Ser Gly
130                 135                 140

Gly Gly Gly Ser Gly Gly Gly Gly Ser Gly Gly Gly Gly Ser Asp Ile
145                 150                 155                 160

Gln Leu Thr Gln Ser Pro Asp Ser Leu Ala Val Ser Leu Gly Glu Arg
                 165                 170                 175

Ala Thr Ile Asn Cys Lys Ser Ser Gln Ser Val Leu Tyr Ser Ser Ile
             180                 185                 190

Asn Lys Asn Tyr Leu Ala Trp Tyr Gln Gln Lys Pro Gly Gln Pro Pro
         195                 200                 205

Lys Leu Leu Ile Tyr Trp Ala Ser Thr Arg Glu Ser Gly Val Pro Asp
 210                 215                 220

Arg Phe Ser Gly Ser Gly Ser Gly Thr Asp Phe Thr Leu Thr Ile Ser
225                 230                 235                 240

Ser Leu Gln Ala Glu Asp Val Ala Val Tyr Tyr Cys Gln Gln Tyr Tyr
                 245                 250                 255

Ser Thr Pro Tyr Thr Phe Gly Gln Gly Thr Lys Val Glu Ile Lys Ser
             260                 265                 270

Tyr Val Thr Val Ser Ser Gln Asp Pro Ala Glu Pro Lys Ser Pro Asp
         275                 280                 285

Lys Thr His Thr Cys Pro Pro Cys Pro Ala Pro Glu Leu Leu Gly Gly
 290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Val Asp Val Ser His Glu
                 325                 330                 335

Asp Pro Glu Val Lys Phe Asn Trp Tyr Val Asp Gly Val Glu Val His
             340                 345                 350

Asn Ala Lys Thr Lys Pro Arg Glu Glu Gln Tyr Asn Ser Thr Tyr Arg
         355                 360                 365

Val Val Ser Val Leu Thr Val Leu His Gln Asp Trp Leu Asn Gly Lys
 370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                 405                 410                 415

Thr Leu Pro Pro Ser Arg Asp Glu Leu Thr Lys Asn Gln Val Ser Leu
             420                 425                 430
```

```
Thr Cys Leu Val Lys Gly Phe Tyr Pro Ser Asp Ile Ala Val Glu Trp
            435                 440                 445
Glu Ser Asn Gly Gln Pro Glu Asn Asn Tyr Lys Thr Thr Pro Pro Val
        450                 455                 460
Leu Asp Ser Asp Gly Ser Phe Phe Leu Tyr Ser Lys Leu Thr Val Asp
465                 470                 475                 480
Lys Ser Arg Trp Gln Gln Gly Asn Val Phe Ser Cys Ser Val Met His
                485                 490                 495
Glu Ala Leu His Asn His Tyr Thr Gln Lys Ser Leu Ser Leu Ser Pro
            500                 505                 510
Gly Lys Lys Asp Pro Lys Phe Trp Val Leu Val Val Val Gly Gly Val
        515                 520                 525
Leu Ala Cys Tyr Ser Leu Leu Val Thr Val Ala Phe Ile Ile Phe Trp
530                 535                 540
Val Arg Ser Lys Arg Ser Arg Leu Leu His Ser Asp Tyr Met Asn Met
545                 550                 555                 560
Thr Pro Arg Arg Pro Gly Pro Thr Arg Lys His Tyr Gln Pro Tyr Ala
                565                 570                 575
Pro Pro Arg Asp Phe Ala Ala Tyr Arg Ser Lys Arg Gly Arg Lys Lys
            580                 585                 590
Leu Leu Tyr Ile Phe Lys Gln Pro Phe Met Arg Pro Val Gln Thr Thr
        595                 600                 605
Gln Glu Glu Asp Gly Cys Ser Cys Arg Phe Pro Glu Glu Glu Glu Gly
            610                 615                 620
Gly Cys Glu Leu Arg Val Lys Phe Ser Arg Ser Ala Asp Ala Pro Ala
625                 630                 635                 640
Tyr Gln Gln Gly Gln Asn Gln Leu Tyr Asn Glu Leu Asn Leu Gly Arg
                645                 650                 655
Arg Glu Glu Tyr Asp Val Leu Asp Lys Arg Arg Gly Arg Asp Pro Glu
            660                 665                 670
Met Gly Gly Lys Pro Arg Arg Lys Asn Pro Gln Glu Gly Leu Tyr Asn
        675                 680                 685
Glu Leu Gln Lys Asp Lys Met Ala Glu Ala Tyr Ser Glu Ile Gly Met
690                 695                 700
Lys Gly Glu Arg Arg Arg Gly Lys Gly His Asp Gly Leu Tyr Gln Gly
705                 710                 715                 720
Leu Ser Thr Ala Thr Lys Asp Thr Tyr Asp Ala Leu His Met Gln Ala
                725                 730                 735
Leu Pro Pro Arg
            740

<210> SEQ ID NO 4
<211> LENGTH: 2223
<212> TYPE: DNA
<213> ORGANISM: Artificial Sequence
<220> FEATURE:
<223> OTHER INFORMATION: CR3022 CAR sequence

<400> SEQUENCE: 4
atggagtttg ggctgagctg gcttttttctt gtggctattt taaaaggtgt ccagtgcgtc      60
gaccagatgc agctggtgca atctggaaca gaggtgaaaa agccggggga gtctctgaag     120
atctcctgta agggttctgg atacggcttt atcacctact ggatcggctg ggtgcgccag     180
atgcccggga aaggcctgga gtggatgggg atcatctatc ctggtgactc tgaaaccaga     240
tacagcccgt ccttccaagg ccaggtcacc atctcagccg acaagtccat caacaccgcc     300
```

```
tacctgcagt ggagcagcct gaaggcctcg acaccgcca tatattactg tgcgggggt      360
tcggggattt ctaccctat ggacgtctgg ggccaaggga ccacggtcac cgtcggtggt     420
ggtggttctg gtggtggtgg ttctggcggc ggcggctccg gtggtggtgg atccgacatc   480
cagttgaccc agtctccaga ctccctggct gtgtctctgg gcgagagggc caccatcaac   540
tgcaagtcca gccagagtgt tttatacagc tccatcaata gaaactactt agcttggtac   600
cagcagaaac caggacagcc tcctaagctg ctcatttact gggcatctac ccgggaatcc   660
ggggtccctg accgattcag tggcagcggg tctgggacag atttcactct caccatcagc   720
agcctgcagg ctgaagatgt ggcagtttat tactgtcagc aatattatag tactccgtac   780
acttttggcc aggggaccaa ggtggaaatc aaatcgtacg tcaccgtctc ttcacaggat   840
cccgccgagc ccaaatctcc tgacaaaact cacacatgcc caccgtgccc agcacctgaa   900
ctcctggggg gaccgtcagt cttcctcttc ccccaaaac ccaaggacac cctcatgatc    960
tcccggaccc ctgaggtcac atgcgtggtg gtggacgtga gccacgaaga ccctgaggtc   1020
aagttcaact ggtacgtgga cggcgtggag gtgcataatg ccaagacaaa gccgcgggag   1080
gagcagtaca acagcacgta ccgtgtggtc agcgtcctca ccgtcctgca ccaggactgg   1140
ctgaatggca aggagtacaa gtgcaaggtc tccaacaaag ccctcccagc ccccatcgag   1200
aaaaccatct ccaaagccaa agggcagccc cgagaaccac aggtgtacac cctgccccca   1260
tcccgggatg agctgaccaa gaaccaggtc agcctgacct gcctggtcaa aggcttctat   1320
cccagcgaca tcgccgtgga gtgggagagc aatgggcaac ggagaacaa ctacaagacc    1380
acgcctcccg tgctggactc cgacggctcc ttcttcctct acagcaagct caccgtggac   1440
aagagcaggt ggcagcaggg gaacgtcttc tcatgctccg tgatgcatga ggctctgcac   1500
aaccactaca cgcagaagag cctctccctg tctccgggta aaaaagatcc caaattttgg   1560
gtgctggtgg tggttggtgg agtcctggct tgctatagct tgctagtaac agtggccttt   1620
attattttt gggtgaggag taagaggagc aggctcctgc acagtgacta catgaacatg   1680
actccccgcc gccccgggcc caccgcaag cattaccagc cctatgcccc accacgcgac    1740
ttcgcagcct atcgctccaa acggggcaga agaaactcc tgtatatatt caaacaacca    1800
tttatgagac cagtacaaac tactcaagag gaagatggct gtagctgccg atttccagaa   1860
gaagaagaag aggatgtga actgagagtg aagttcagca ggagcgcaga cgccccgcg    1920
taccagcagg ccagaaccca gctctataac gagctcaatc taggacgaag agaggagtac   1980
gatgtttgg acaagagacg tggccgggac cctgagatgg ggggaaagcc gagaaggaag    2040
aaccctcagg aaggcctgta caatgaactg cagaaagata gatggcgga ggcctacagt     2100
gagattggga tgaaaggcga gcgccggagg ggcaaggggc acgatggcct ttaccagggt   2160
ctcagtacag ccaccaagga cacctacgac gcccttcaca tgcaggccct gccccctcgc   2220
taa                                                                 2223
```

<210> SEQ ID NO 5
<211> LENGTH: 117
<212> TYPE: PRT
<213> ORGANISM: Artificial Sequence
<220> FEATURE:
<223> OTHER INFORMATION: CR3022 VH domain sequence

<400> SEQUENCE: 5

Gln Met Gln Leu Val Gln Ser Gly Thr Glu Val Lys Lys Pro Gly Glu
1               5                   10                  15

Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Gly Gly Ser Gly Ile Ser Thr Pro Met Asp Val Trp Gly Gln Gly
            100                 105                 110

Thr Thr Val Thr Val
        115

<210> SEQ ID NO 6
<211> LENGTH: 351
<212> TYPE: DNA
<213> ORGANISM: Artificial Sequence
<220> FEATURE:
<223> OTHER INFORMATION: CR3022 VH domain

<400> SEQUENCE: 6
cagatgcagc tggtgcaatc tggaacagag gtgaaaaagc cgggggagtc tctgaagatc      60
tcctgtaagg gttctggata cggctttatc acctactgga tcggctgggt gcgccagatg     120
cccgggaaag cctggagtg atgggatc atctatcctg gtgactctga aaccagatac        180
agcccgtcct tccaaggcca ggtcaccatc tcagccgaca gtccatcaa caccgcctac      240 ctgcagtgga gcagcctgaa ggcctcggac accgccatat attactgtgc ggggggttcg     300
gggatttcta ccccctatgga cgtctggggc caagggacca cggtcaccgt c             351

<210> SEQ ID NO 7
<211> LENGTH: 113
<212> TYPE: PRT
<213> ORGANISM: Artificial Sequence
<220> FEATURE:
<223> OTHER INFORMATION: CR3022 VL domain

<400> SEQUENCE: 7

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys

<210> SEQ ID NO 8

```
<211> LENGTH: 339
<212> TYPE: DNA
<213> ORGANISM: Artificial Sequence
<220> FEATURE:
<223> OTHER INFORMATION: CR3022 VL domain

<400> SEQUENCE: 8
gacatccagt tgacccagtc tccagactcc ctggctgtgt ctctgggcga gagggccacc      60
atcaactgca agtccagcca gagtgtttta tacagctcca tcaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
ccgtacactt ttggccaggg gaccaaggtg gaaatcaaa                            339
```

CR3022 CHIMERIC ANTIGEN RECEPTORS AND METHODS OF USE

CROSS REFERENCE TO RELATED APPLICATIONS

This application claims the benefit of U.S. Provisional Application No. 63/064,156, filed Aug. 11, 2020, which is incorporated herein by reference in its entirety.

ACKNOWLEDGMENT OF GOVERNMENT SUPPORT

This invention was made with government support under grant number 1R01AI130197-01A1 awarded by the National Institutes of Health. The government has certain rights in the invention.

FIELD

This disclosure relates to chimeric antigen receptors, particularly chimeric antigen receptors targeting coronavirus spike protein, and methods of their use for treating coronavirus infection.

BACKGROUND

SARS-CoV-2 is highly contagious and presents a significant public health issue. Current treatment for COVID-19 patients can be classified into three categories: anti-viral treatments, immunosuppression-based treatments, and other supporting treatments such as convalescent plasma. Specifically, in a few trials patients have been given combinations of antivirals including umifenovir, remdesivir/ribavirin, chloroquine (an anti-malarial drug), the chloroquine analogue hydroxychloroquine (a disease-modifying antirheumatic drug), and/or lopinavir/ritonavir. Non-steroidal anti-inflammatory drugs (NSAIDs), antibodies against IL-6 receptors, and corticosteroids have also been used during the early acute phase of SARS-CoV-2 to suppress the overactivated immune response. Other supporting therapies include supplemental oxygen and mechanical ventilatory support when indicated (e.g., intubation).

SUMMARY

There remains a need to develop additional effective treatments for COVID-19 and disease caused by other coronaviruses. Disclosed herein are chimeric antigen receptors (CARs) including an antigen binding domain (such as a scFv) of antibody CR3022 and methods of their use for treating a subject with coronavirus disease (such as COVID-19). Also disclosed are CR3022-CAR-natural killer (NK) cells that can specifically bind to the receptor binding domain (RBD) of SARS-CoV-2 and pseudotyped SARS-CoV-2 spike (S) protein, and can be activated by pseudotyped SARS-CoV-2-S viral particles in vitro. Further, CR3022-CAR-NK cells can specifically kill pseudo-SARS-CoV-2 infected target cells.

In some embodiments, disclosed is a chimeric antigen receptor including an antigen binding domain that specifically binds coronavirus spike protein, including an amino acid sequence including variable heavy chain (VH) domain complementarity determining region 1 (CDR1), CDR2 and CDR3 amino acid sequences of amino acid positions 31-34, 50-66, and 99-108 of SEQ ID NO: 1, respectively, and variable light chain (VL) domain CDR1, CDR2 and CDR3 amino acid sequences of amino acid positions 161-177, 193-199, and 232-240 of SEQ ID NO: 1, respectively; a hinge domain; a transmembrane domain; and an intracellular domain.

In some embodiments, the chimeric antigen receptor includes a VH domain that has at least 90% sequence identity to the amino acid sequence of SEQ ID NO: 5, a VL domain that has at least 90% sequence identity to the amino acid sequence of SEQ ID NO: 7, or both. In other embodiments, the chimeric antigen receptor includes an antigen binding domain that has at least 90% sequence identity to the amino acid sequence of SEQ ID NO: 1. In other examples, the chimeric antigen receptor includes an antigen binding domain that includes or consists of the amino acid sequence of SEQ ID NO: 1.

In one embodiment, the hinge domain of the CAR includes an IgG1 domain, the transmembrane domain includes a CD28 transmembrane domain, and the intracellular domain includes a CD28 domain, a 4-1BB domain, and a CD3ζ domain. In some examples, the chimeric antigen receptor has at least 90% sequence identity to the amino acid sequence of SEQ ID NO: 3. In other examples, the chimeric antigen receptor includes or consists of the amino acid sequence of SEQ ID NO: 3.

In additional embodiments, the chimeric antigen receptor further includes one or more additional antigen binding domains, for example, one or more additional antigen binding domains that specifically bind coronavirus spike protein. In some examples, the additional antigen binding domain that specifically binds coronavirus spike protein is different from the first antigen binding domain (e.g., is different from SEQ ID NO: 1). In other embodiments, the chimeric antigen receptor, further comprises an inducible suicide molecule (such as an inducible caspase 9).

Nucleic acids encoding the disclosed chimeric antigen receptors are also provided. In some embodiments, the nucleic acid has at least 90% sequence identity to the nucleic acid sequence of SEQ ID NO: 4. In other embodiments, the nucleic acid includes or consists of the nucleic acid sequence of SEQ ID NO: 4. Also provided are vectors including the disclosed nucleic acids, for example, a viral vector including a nucleic acid encoding a disclosed CAR.

Also provided are modified immune cells (such as T cells, natural killer (NK) cells, NKT cells, or macrophages) expressing the disclosed chimeric antigen receptors. In some examples, the modified cell is an NK cell, for example, an NK-92 cell or NK-92MI cell.

Methods of treating a subject with a coronavirus infection are also provided. In some embodiments, the methods include administering an effective amount of a modified immune cell expressing a disclosed CAR to the subject. In particular examples, the subject is infected with SARS-CoV-1 or SARS-CoV-2.

The foregoing and other features of the disclosure will become more apparent from the following detailed description, which proceeds with reference to the accompanying figures.

BRIEF DESCRIPTION OF THE DRAWINGS

FIG. 1A: Schematic design of CR3022-CAR in SFG retroviral vector. The SFG retroviral vector contains the CR3022 single chain antibody fragment (clone 3), a human IgG1 CH2CH3 hinge region and CD28 transmembrane region, followed by the intracellular domains of co-stimulatory CD28, 4-1BB, and the intracellular domain of CD3ζ. FIG. 1B: Generation of CR3022-CAR-NK cells. 293T cells were transfected with SFG-CR3022-CAR for 48-72 hours for CAR retrovirus packaging and transduced into NK92MI cells. FIG. 1C: Determination of CAR expression by flow cytometry. CR3022-CAR cells were harvested after 4-5 days then stained with anti-CD56 and CAR F(ab)2 domain [IgG (H+L)] for flow cytometry.

FIG. 2A: Immunophenotyping of CR3022-CAR. Antibodies against various immunomodulatory receptors including TIGIT, LAG-3, TIM-3, KLRG1, CTLA-4, PD-1, CD69, CD8A, NKG2C, CD94, DNAM-1, 2B4, NKG2D, NKP46, and CD16 were used to stain CR3022-CAR and NK-92MI cells. The expression of these receptors was determined by flow cytometry. FMO: fluorescence minus one. FMO is a sample of cells stained with all fluorochromes used in the experiment except one. FIG. 2B: Schematic diagram of CR3022-CAR binding to the RBD domain of SARS-CoV-2-S recombinant protein. CR3022-CAR binds to RBD of SARS-CoV-2-S protein, which is then recognized by anti-His and its corresponding secondary antibody conjugated to a fluorophore. FIG. 2C: Representative dot plots of CR3022-CAR binding to RBD of SARS-CoV-2. CR3022-CAR or NK-92MI cells were incubated with SARS-CoV-2-RBD or SARS-CoV-1-RBD recombinant protein. The binding efficiency was determined by flow cytometry.

FIGS. 3A-3C show CR3022-CAR-NK-92MI cells binding to pseudotyped SARS-CoV-2-S viral particles. FIG. 3A: Schematic diagram of CR3022-CAR binding to pseudotyped SARS-CoV-2-S viral particles. CR3022-CAR binds to pseudotyped SARS-CoV-2-S viral particle, which is then recognized by anti-spike and its corresponding secondary antibody conjugated to a fluorophore. FIG. 3B: Representative histogram of CR3022-CAR binding to pseudotyped SARS-CoV-2-S. CR3022-CAR or NK-92MI or 293T-hACE2 cells were incubated with pseudotyped SARS-CoV-2 or full-length spike or S1 subunit recombinant protein. The binding efficiency was determined by flow cytometry. Experimental sample was performed in triplicate with MFI 6759±440 (a.u.). FIG. 3C: Graph showing the binding efficiency of CR3022-CAR to pseudotyped SARS-CoV-2-S. The values were converted from FIG. 3B. Experimental sample was performed in triplicate with binding efficiency 51.4±3.34(%).

FIGS. 4A-4D show increased CD107a degranulation and killing activity of CR3022-CAR-NK-92MI cells against 293T-hACE2 cells transfected with RBD-SARS-Cov-2 Spike. FIG. 4A: 293T-hACE2 cells were transfected with a plasmid containing firefly luciferase and GFP as well as SARS-CoV-2 Spike protein receptor binding domain for 48 hours. FIG. 4B: Successful transfection was confirmed by flow cytometry using anti-RBD antibody. Cells were then harvested and used as target cells for subsequent CD107a degranulation assay and luciferase killing assays. FIG. 4C: Representative dot plots of CD107a assay and quantitative data of the percentage and mean fluorescence intensity of CD107a positive CR3022-CAR-NK92MI cells are shown. FIG. 4D: Quantitative data of the luciferase killing assay using CR3022-CAR-NK92MI and wild-type NK-92MI cells against 293T-hACE2-FFLuc-GFP-RBD cells is shown. Experimental groups were performed in triplicate. *p<0.05, p<0.01, *p=0.001, ****p<0.0001 ns p>0.05. Data represent the mean±SEM from at least two independent experiments. Briefly, 5×10$^4$ CR3022-CAR-NK92MI cells were cocultured with either 1×10$^5$ RBD transfected-293T-hACE2 cells, 293T-hACE2 cells, stimulated with PMA/Ionomycin, or incubated alone for 2 hours at 37° C. Then, cells were harvested, stained for CAR F(ab)2 domain [IgG (H+L)], and CD107a. Representative flow cytometry dot plots, CD107a percent of total CAR cells, and CD107a MFI are shown.

FIGS. 5A-5C show increased killing activity of CR3022-CAR-NK-92MI cells against 293T-hACE2 cells transfected with SARS-Cov-2 Spike protein Receptor Binding Domain using the $^{51}$Cr release platform. FIG. 5A: 293T-hACE2 cells were transfected with SARS-Cov-2 Spike protein receptor binding domain for 48 hours. FIG. 5B: Successful transfection was confirmed by flow cytometry using Anti-RBD antibody. Cells were then harvested and used as target cells for the subsequent $^{51}$Cr release assay. FIG. 5C: Quantitative data of the $^{51}$Cr release assay using CR3022-CAR-NK-92MI cells and wild-type NK-92MI cells. Experimental groups were performed in triplicate. *p<0.05, p<0.01, *p=0.001, ****p<0.0001 ns p>0.05. Data represent the mean±SEM from at least two independent experiments.

SEQUENCE LISTING

Figure 1A:
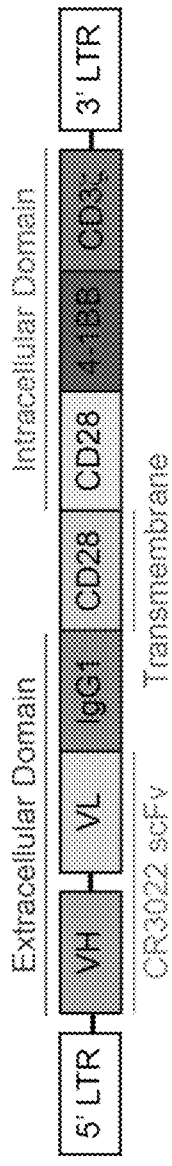
FIGS. 1A-1C show generation of CR3022-CAR-NK92MI cells.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Aug. 11, 2021, and is 16,149 bytes, which is incorporated by reference herein.

```
SEQ ID NO: 1 is the amino acid sequence of a
CR3022 scFv:
QMQLVQSGTEVKKPGESLKISCKGSGYGFITYWIGWVRQMPGKGLEWMG

IIYPGDSETRYSPSFQGQVTISADKSINTAYLQWSSLKASDTAIYYCAG

GSGISTPMDVWGQGTTVTVGGGGSGGGGSGGGGSGGGGSDIQLTQSPDS

LAVSLGERATINCKSSQSVLYSSINKNYLAWYQQKPGQPPKLLIYWAST

RESGVPDRFSGSGSGTDFTLTISSLQAEDVAVYYCQQYYSTPYTFGQGT

KVEIK

SEQ ID NO: 2 is a nucleic acid sequence encoding
a CR3022 scFv:
CAGATGCAGCTGGTGCAATCTGGAACAGAGGTGAAAAAGCCGGGGGAGT

CTCTGAAGATCTCCTGTAAGGGTTCTGGATACGGCTTTATCACCTACTG

GATCGGCTGGGTGCGCCAGATGCCCGGGAAAGGCCTGGAGTGGATGGGG

ATCATCTATCCTGGTGACTCTGAAACCAGATACAGCCCGTCCTTCCAAG

GCCAGGTCACCATCTCAGCCGACAAGTCCATCAACACCGCCTACCTGCA

GTGGAGCAGCCTGAAGGCCTCGGACACCGCCATATATTACTGTGCGGGG

GGTTCGGGGATTTCTACCCCTATGGACGTCTGGGGCCAAGGGACCACGG

TCACCGTCGGTGGTGGTGGTTCTGGTGGTGGTGGTTCTGGCGGCGGCGG

CTCCGGTGGTGGTGGATCCGACATCCAGTTGACCCAGTCTCCAGACTCC

CTGGCTGTGTCTCTGGGCGAGAGGGCCACCATCAACTGCAAGTCCAGCC

AGAGTGTTTTATACAGCTCCATCAATAAGAACTACTTAGCTTGGTACCA

GCAGAAACCAGGACAGCCTCCTAAGCTGCTCATTTACTGGGCATCTACC
```

```
-continued
CGGGAATCCGGGGTCCCTGACCGATTCAGTGGCAGCGGGTCTGGGACAG

ATTTCACTCTCACCATCAGCAGCCTGCAGGCTGAAGATGTGGCAGTTTA

TTACTGTCAGCAATATTATAGTACTCCGTACACTTTTGGCCAGGGGACC

AAGGTGGAAATCAAA

SEQ ID NO: 3 is the amino acid sequence of an
exemplary CR3022-CAR:
MEFGLSWLFLVAILKGVQCVDQMQLVQSGTEVKKPGESLKISCKGSGYG

FITYWIGWVRQMPGKGLEWMGIIYPGDSETRYSPSFQGQVTISADKSIN

TAYLQWSSLKASDTAIYYCAGGSGISTPMDVWGQGTTVTVGGGGSGGGG

SGGGGSGGGGSDIQLTQSPDSLAVSLGERATINCKSSQSVLYSSINKNY

LAWYQQKPGQPPKLLIYWASTRESGVPDRFSGSGSGTDFTLTISSLQAE

DVAVYYCQQYYSTPYTFGQGTKVEIKSYVTVSSQDPAEPKSPDKTHTCP

PCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVF

SCSVMHEALHNHYTQKSLSLSPGKKDPKFWVLVVVGGVLACYSLLVTVA

FIIFWVRSKRSRLLHSDYMNMTPRRPGPTRKHYQPYAPPRDFAAYRSKR

GRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQ

ALPPR

SEQ ID NO: 4 is a nucleic acid sequence encoding
an exemplary CR3022-CAR:
ATGGAGTTTGGGCTGAGCTGGCTTTTTCTTGTGGCTATTTTAAAAGGTG

TCCAGTGCGTCGACCAGATGCAGCTGGTGCAATCTGGAACAGAGGTGAA

AAAGCCGGGGAGTCTCTGAAGATCTCCTGTAAGGGTTCTGGATACGGC

TTTATCACCTACTGGATCGGCTGGGTGCGCCAGATGCCCGGGAAAGGCC

TGGAGTGGATGGGGATCATCTATCCTGGTGACTCTGAAACCAGATACAG

CCCGTCCTTCCAAGGCCAGGTCACCATCTCAGCCGACAAGTCCATCAAC

ACCGCCTACCTGCAGTGGAGCAGCCTGAAGGCCTCGGACACCGCCATAT

ATTACTGTGCGGGGGGTTCGGGGATTTCTACCCCTATGGACGTCTGGGG

CCAAGGGACCACGGTCACCGTCGGTGGTGGTGGTTCTGGTGGTGGTGGT

TCTGGCGGCGGCGGCTCCGGTGGTGGTGGATCCGACATCCAGTTGACCC

AGTCTCCAGACTCCCTGGCTGTGTCTCTGGGCGAGAGGGCCACCATCAA

CTGCAAGTCCAGCCAGAGTGTTTTATACAGCTCCATCAATAAGAACTAC

TTAGCTTGGTACCAGCAGAAACCAGGACAGCCTCCTAAGCTGCTCATTT

ACTGGGCATCTACCCGGGAATCCGGGGTCCCTGACCGATTCAGTGGCAG

CGGGTCTGGGACAGATTTCACTCTCACCATCAGCAGCCTGCAGGCTGAA

GATGTGGCAGTTTATTACTGTCAGCAATATTATAGTACTCCGTACACTT

TTGGCCAGGGGACCAAGGTGGAAATCAAATCGTACGTCACCGTCTCTTC

ACAGGATCCCGCCGAGCCCAAATCTCCTGACAAAACTCACACATGCCCA

CCGTGCCCAGCACCTGAACTCCTGGGGGGACCGTCAGTCTTCCTCTTCC

-continued
CCCCAAAACCCAAGGACACCCTCATGATCTCCCGGACCCCTGAGGTCAC

ATGCGTGGTGGTGGACGTGAGCCACGAAGACCCTGAGGTCAAGTTCAAC

TGGTACGTGGACGGCGTGGAGGTGCATAATGCCAAGACAAAGCCGCGGG

AGGAGCAGTACAACAGCACGTACCGTGTGGTCAGCGTCCTCACCGTCCT

GCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGC

AGCCCCGAGAACCACAGGTGTACACCCTGCCCCCATCCCGGGATGAGCT

GACCAAGAACCAGGTCAGCCTGACCTGCCTGGTCAAAGGCTTCTATCCC

AGCGACATCGCCGTGGAGTGGGAGAGCAATGGGCAACCGGAGAACAACT

ACAAGACCACGCCTCCCGTGCTGGACTCCGACGGCTCCTTCTTCCTCTA

CAGCAAGCTCACCGTGGACAAGAGCAGGTGGCAGCAGGGGAACGTCTTC

TCATGCTCCGTGATGCATGAGGCTCTGCACAACCACTACACGCAGAAGA

GCCTCTCCCTGTCTCCGGGTAAAAAGATCCCAAATTTTGGGTGCTGGT

GGTGGTTGGTGGAGTCCTGGCTTGCTATAGCTTGCTAGTAACAGTGGCC

TTTATTATTTTTTGGGTGAGGAGTAAGAGGAGCAGGCTCCTGCACAGTG

ACTACATGAACATGACTCCCCGCCGCCCCGGGCCCACCCGCAAGCATTA

CCAGCCCTATGCCCCACCACGCGACTTCGCAGCCTATCGCTCCAAACGG

GGCAGAAAGAAACTCCTGTATATATTCAAACAACCATTTATGAGACCAG

TACAAACTACTCAAGAGGAAGATGGCTGTAGCTGCCGATTTCCAGAAGA

AGAAGAAGGAGGATGTGAACTGAGAGTGAAGTTCAGCAGGAGCGCAGAC

GCCCCCGCGTACCAGCAGGGCCAGAACCAGCTCTATAACGAGCTCAATC

TAGGACGAAGAGAGGAGTACGATGTTTTGGACAAGAGACGTGGCCGGGA

CCCTGAGATGGGGGGAAAGCCGAGAAGGAAGAACCCTCAGGAAGGCCTG

TACAATGAACTGCAGAAAGATAAGATGGCGGAGGCCTACAGTGAGATTG

GGATGAAAGGCGAGCGCCGGAGGGGCAAGGGGCACGATGGCCTTTACCA

GGGTCTCAGTACAGCCACCAAGGACACCTACGACGCCCTTCACATGCAG

GCCCTGCCCCCTCGCTAA

SEQ ID NO: 5 is the amino acid sequence of a
CR3022 VH domain:
QMQLVQSGTEVKKPGESLKISCKGSGYGFITYWIGWVRQMPGKGLEWMG

IIYPGDSETRYSPSFQGQVTISADKSINTAYLQWSSLKASDTAIYYCAG

GSGISTPMDVWGQGTTVTV

SEQ ID NO: 6 is the nucleic acid sequence of a
CR3022 VH domain:
CAGATGCAGCTGGTGCAATCTGGAACAGAGGTGAAAAAGCCGGGGAGT

CTCTGAAGATCTCCTGTAAGGGTTCTGGATACGGCTTTATCACCTACTG

GATCGGCTGGGTGCGCCAGATGCCCGGGAAAGGCCTGGAGTGGATGGGG

ATCATCTATCCTGGTGACTCTGAAACCAGATACAGCCCGTCCTTCCAAG

GCCAGGTCACCATCTCAGCCGACAAGTCCATCAACACCGCCTACCTGCA

GTGGAGCAGCCTGAAGGCCTCGGACACCGCCATATATTACTGTGCGGGG

GGTTCGGGGATTTCTACCCCTATGGACGTCTGGGGCCAAGGGACCACGG

TCACCGTC
```

-continued

SEQ ID NO: 7 is the amino acid sequence of a
CR3022 VL domain:
DIQLTQSPDSLAVSLGERATINCKSSQSVLYSSINKNYLAWYQQKPGQP

PKLLIYWASTRESGVPDRFSGSGSGTDFTLTISSLQAEDVAVYYCQQYY

STPYTFGQGTKVEIK

SEQ ID NO: 8 is the nucleic acid sequence of a
CR3022 VL domain:
GACATCCAGTTGACCCAGTCTCCAGACTCCCTGGCTGTGTCTCTGGGCG

AGAGGGCCACCATCAACTGCAAGTCCAGCCAGAGTGTTTTATACAGCTC

CATCAATAAGAACTACTTAGCTTGGTACCAGCAGAAACCAGGACAGCCT

CCTAAGCTGCTCATTTACTGGGCATCTACCCGGGAATCCGGGGTCCCTG

ACCGATTCAGTGGCAGCGGGTCTGGGACAGATTTCACTCTCACCATCAG

CAGCCTGCAGGCTGAAGATGTGGCAGTTTATTACTGTCAGCAATATTAT

AGTACTCCGTACACTTTTGGCCAGGGGACCAAGGTGGAAATCAAA

DETAILED DESCRIPTION

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are any GenBank Accession numbers (as present in the database on Aug. 10, 2021). In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used. In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Chimeric antigen receptor (CAR): A chimeric molecule that includes an antigen-binding portion (such as a single domain antibody or scFv) and a signaling domain, such as a signaling domain from a T cell receptor (e.g. CD3ζ). Typically, CARs include an antigen-binding portion, a transmembrane domain, and an intracellular domain. The intracellular domain typically includes a signaling domain having an immunoreceptor tyrosine-based activation motif (ITAM), such as CD3ζ or FcεRIγ. In some instances, the intracellular domain also includes the intracellular portion of at least one additional co-stimulatory domain, such as CD28, 4-1BB (CD137), ICOS, OX40 (CD134), CD27, and/or DAP10.

Complementarity determining region (CDR): A region of hypervariable amino acid sequence that defines the binding affinity and specificity of an antibody. The light and heavy chains of a mammalian immunoglobulin each have three CDRs, designated VL-CDR1, VL-CDR2, VL-CDR3 and VH-CDR1, VH-CDR2, VH-CDR3, respectively.

Coronavirus: Coronaviruses are a large family of positive-sense, single-stranded RNA viruses that can infect humans and non-human animals. The viral envelope is composed of a lipid bilayer containing the viral membrane (M), envelope (E) and spike (S) proteins. Most coronaviruses cause mild to moderate upper respiratory tract illness; however, three coronaviruses have emerged that can cause more serious illness and death in humans. These are two severe acute respiratory syndrome coronaviruses (SARS-CoV and SARS-CoV-2) and Middle East respiratory syndrome coronavirus (MERS-CoV). Other coronaviruses that infect humans include human coronavirus HKU1, human coronavirus OC43, human coronavirus 229E, and human coronavirus NL63.

Isolated: An "isolated" biological component, such as a nucleic acid, protein, or cell, has been substantially separated or purified away from other biological components in the environment in which the component initially occurs, e.g., other cells, chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down-regulating MHC class I presentation. In addition to being involved in direct cytotoxic killing, NK cells also serve a role in cytokine production, which can be important to control cancer and infection.

In some examples, a "modified NK cell" is a NK cell transduced or transfected with a heterologous nucleic acid (such as one or more of the nucleic acids or vectors disclosed herein) or expressing one or more heterologous proteins. The terms "modified NK cell" and "transduced NK cell" are used interchangeably in some examples herein.

Pharmaceutically acceptable carriers: *Remington: The Science and Practice of Pharmacy*, 22$^{nd}$ ed., London, UK: Pharmaceutical Press (2013), describes compositions and formulations suitable for pharmaceutical delivery of modified immune cells and other compositions disclosed herein. In general, the nature of the carrier will depend on the particular mode of administration being employed. For instance, parenteral formulations usually include pharmaceutically and physiologically acceptable fluids such as water, physiological saline, balanced salt solutions, aqueous dextrose, glycerol or the like as a vehicle. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term purified does not require absolute purity; rather, it is intended as a relative term. Thus, for example, a purified protein, nucleic acid, or cell preparation is one in which the protein, nucleic acid, or cell is more enriched than in its initial environment. In one embodiment, a preparation is purified such that the protein, nucleic acid, or cell represents at least 50% of the total protein, nucleic acid, or cell content of the preparation. Substantial purification denotes purification from other proteins, nucleic acids, or cells. A substantially purified protein, nucleic acid, or cell is at least 60%, 70%, 80%, 90%, 95%, 98%, or 99% pure. Thus, in one specific, non-limiting example, a substantially purified protein, nucleic acid, or cell is 90% free of other components.

Recombinant: A nucleic acid or protein that has a sequence that is not naturally occurring or has a sequence that is made by an artificial combination of two otherwise separated segments of sequence (e.g., a "chimeric" sequence). This artificial combination can be accomplished by chemical synthesis or by the artificial manipulation of isolated segments of nucleic acids, for example, by genetic engineering techniques.

SARS-CoV-2: A virus of the genus betacoronavirus that first emerged in humans in 2019, also referred to as Wuhan coronavirus, 2019-nCoV, or 2019 novel coronavirus. Symptoms of SARS-CoV-2 infection include fever, chills, dry cough, shortness of breath, fatigue, muscle/body aches, headache, new loss of taste or smell, sore throat, nausea or vomiting, and diarrhea. Patients with severe disease can develop pneumonia, multi-organ failure, and death. The SARS-CoV-2 virion includes a viral envelope with large spike glycoproteins. The SARS-CoV-2 genome encodes a canonical set of structural protein genes in the order 5'-spike (S)-envelope (E)-membrane (M)-nucleocapsid (N)-3'.

Spike (S) protein: A class I fusion glycoprotein initially synthesized as a precursor protein of approximately 1256 amino acids for SARS-CoV, and 1273 amino acids for SARS-CoV-2. Individual precursor S polypeptides form a homotrimer and undergo glycosylation and processing to remove the signal peptide, and cleavage by a cellular protease between approximately position 679/680 for SARS-CoV, and 685/686 for SARS-CoV-2, to generate separate S1 and S2 polypeptide chains, which remain associated as S1/S2 protomers within the homotrimer, thereby forming a trimer of heterodimers. The S1 subunit is distal to the virus membrane and contains the receptor-binding domain (RBD) that is believed to mediate virus attachment to its host receptor. The S2 subunit is believed to contain the fusion protein machinery, such as the fusion peptide. S2 also includes two heptad-repeat sequences (HR1 and HR2) and a central helix typical of fusion glycoproteins, a transmembrane domain, and a cytosolic tail domain. An exemplary SARS-CoV-2 spike protein sequence includes GenBank Accession No. QHD43416.1 (the sequence of which is incorporated by reference herein).

Subject: A living multi-cellular vertebrate organism, a category that includes both human and veterinary subjects, including human and non-human mammals.

Transduced or Transformed: A transformed cell is a cell into which a nucleic acid molecule has been introduced by molecular biology techniques. As used herein, the terms transduction and transformation encompass all techniques by which a nucleic acid molecule might be introduced into such a cell, including transfection with viral vectors, the use of plasmid vectors, and introduction of DNA by electroporation, lipofection, and particle gun acceleration.

Treating or ameliorating a disease: "Treating" refers to a therapeutic intervention that decreases or inhibits a sign or symptom of a disease or pathological condition after it has begun to develop "Ameliorating" refers to the reduction in the number or severity of signs or symptoms of a disease, such as that caused by SARS coronaviruses.

Vector: A nucleic acid molecule that can be introduced into a host cell (for example, by transfection or transduction), thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function.

II. CR3022-Chimeric Antigen Receptors

Provided herein are CARs that include a coronavirus spike protein-specific binding agent. In some embodiments, the CAR includes an antigen binding domain that specifically binds to a coronavirus spike protein, a hinge domain, a transmembrane domain, and an intracellular domain.

In some embodiments, the antigen binding domain includes at least one of the CDR sequences (e.g., at least one of VHCDRs 1-3 and VLCDRs 1-3, such as at least 1, 2, 3, 4, 5, or 6 of the CDR sequences) provided in Table 1, and specifically binds to a coronavirus spike protein. In some embodiments, the antigen binding domain includes the amino acid sequence of each of VHCDR1, VHCDR2, VHCDR3, VLCDR1, VLCDR2, and VLCDR3 as provided in Table 1. In some examples, the antigen binding domain includes an amino acid sequence including variable heavy chain (VH) domain complementarity determining region 1 (CDR1), CDR2 and CDR3 amino acid sequences of amino acid positions 31-34, 50-66, and 99-108 of SEQ ID NO: 1, respectively, and variable light chain (VL) domain CDR1, CDR2 and CDR3 amino acid sequences of amino acid positions 161-177, 193-199, and 232-240 of SEQ ID NO: 1, respectively. In some examples, an antigen binding domain that includes VHCDR1, VHCDR2, VHCDR3, VLCDR1, VLCDR2, and VLCDR3 as provided in Table 1 is referred to as a CR3022 antigen binding domain.

In some embodiments, the chimeric antigen receptor includes a VH domain that has at least 90% sequence identity to the amino acid sequence of SEQ ID NO: 5 (for example, at least 91%, at least 92%, at least 93%, at least 94%, at least 95%, at least 96%, at least 97%, at least 98%, or at least 99% identity) to SEQ ID NO: 5, or including or consisting of the amino acid sequence of SEQ ID NO: 5. In other embodiments, the chimeric antigen receptor includes a VL domain that has at least 90% sequence identity to the amino acid sequence of SEQ ID NO: 7 (for example, at least 91%, at least 92%, at least 93%, at least 94%, at least 95%, at least 96%, at least 97%, at least 98%, or at least 99% identity) to SEQ ID NO: 7, or including or consisting of the amino acid sequence of SEQ ID NO: 7. In one example, the chimeric antigen receptor includes an antigen binding domain that comprises the amino acid sequences of SEQ ID NO: 5 and SEQ ID NO: 7.

In some embodiments, the antigen binding domain is a coronavirus spike protein-specific scFv (for example, from CR3022 antibody), for example having an amino acid sequence with at least 90% sequence identity (for example, at least 91%, at least 92%, at least 93%, at least 94%, at least 95%, at least 96%, at least 97%, at least 98%, or at least 99% identity) to SEQ ID NO: 1, or including or consisting of the amino acid sequence of SEQ ID NO: 1.

TABLE 1

Location of the CDRs in the CR3022 scFv sequence (determined using Kabat method)

| CDR | Nucleic Acid Sequence | Amino Acid Sequence |
|---|---|---|
| VH CDR1 | ACCTACTGGATCGGC (nucleotides 91-105 of SEQ ID NO: 2) | TYWIG (amino acids 31-35 of SEQ ID NO: 1) |
| VH CDR2 | ATCATCTATCCTGGTGACTCT GAAACCAGATACAGCCCGTC CTTCCAAGGC (nucleotides 148-198 of SEQ ID NO: 2) | IIYPGDSETRYSPSFQG (amino acids 50-66 of SEQ ID NO: 1) |
| VH CDR3 | GGTTCGGGGATTTCTACCCCT ATGGACGTC (nucleotides 295-324 of SEQ ID NO: 2) | GSGISTPMDV (amino acids 99-108 of SEQ ID NO: 1) |
| VL CDR1 | AAGTCCAGCCAGAGTGTTTT ATACAGCTCCATCAATAAGA ACTACTTAGCT (nucleotides 481-531 of SEQ ID NO: 2) | KSSQSVLYSSINKNYLA (amino acids 161-177 of SEQ ID NO: 1) |
| VL CDR2 | TGGGCATCTACCCGGGAATC C (nucleotides 577-597 of SEQ IDN O: 2) | WASTRES (amino acids 193-199 of SEQ ID NO: 1) |
| VL CDR3 | CAGCAATATTATAGTACTCC GTACACT (nucleotides 694-720 of SEQ ID NO: 2) | QQYYSTPYT (amino acids 232-240 of SEQ ID NO: 1) |

VHCDR3, VLCDR1, VLCDR2, and VLCDR3 as provided

In some embodiments, the hinge domain is an IgG hinge region. In one example, the hinge domain is an IgG1 hinge. Other hinge domains can be used, such as hinge regions from other immunoglobulins (for example, IgG4 or IgD) or a hinge region from CD8, CD28, or CD40.

In additional embodiments, the transmembrane domain is a CD28 transmembrane domain. In one example, the transmembrane domain is from CD28. The transmembrane domain can also be from other proteins, such as CD8, CD4, CD3ζ, CD40, OX40L, 41BBL, ICOS, ICOS-L, CD80, CD86, ICAM-1, LFA-1, ICAM-1, CD56, CTLA-4, PD-1, TIM-3, NKP30, NKP44, NKP40, NKP46, B7-H3, PD-L1, PD-2, or CD70. In some examples, the hinge domain and transmembrane domain are from different proteins, while in other examples, the hinge domain and transmembrane domain are from the same protein.

In further embodiments, the intracellular domain includes one or more intracellular regions from CD28, 4-1BB, and/or CD3ζ. Other exemplary intracellular regions that can be used include CD8, CD40, OX-40, ICOS, CD27, DAP10, OX40-L, 4-1BBL, ICOS-L, CD80, CD86, ICAM-1, LFA-1, CD56, CTLA-4, PD-1, TIM-3, NKP30, NKP44, NKP40, NKP46, B7-H3, PD-L1, PD-2, CD70, DAP12, PDK, and FcεRIγ.

In some embodiments, the CAR also includes a signal sequence, which is located N-terminal to the antigen binding domain. In some examples, the signal sequence is a IgG signal sequence or a GM-CSF signal sequence. In one example, the CAR includes an IgG signal sequence, for example, amino acids 1-21 of SEQ ID NO: 3.

An exemplary CR3022-CAR is illustrated in FIG. 1A. In one example, the CR3022-CAR has an amino acid sequence with at least 90% sequence identity (for example, at least 91%, at least 92%, at least 93%, at least 94%, at least 95%, at least 96%, at least 97%, at least 98%, or at least 99% sequence identity) to SEQ ID NO: 3, or includes or consists of the amino acid sequence of SEQ ID NO: 3. In another example, the CR3022-CAR has an amino acid sequence with at least 90% sequence identity (for example, at least 91%, at least 92%, at least 93%, at least 94%, at least 95%, at least 96%, at least 97%, at least 98%, or at least 99% sequence identity) to amino acids 22-740 of SEQ ID NO: 3, or includes or consists of the amino acid sequence of amino acids 22-740 of SEQ ID NO: 3.

In some embodiments, the disclosed CARs further include one or more additional antigen binding domains (for example, the CAR is a bispecific CAR or a tri-specific CAR). In some examples, the CAR includes at least one additional antigen binding domain that specifically binds to a coronavirus spike protein or a variant thereof. In some examples, the additional antigen binding domain is different from the CR3022 antigen binding domain. In some examples, the additional antigen binding domain specifically binds to a coronavirus spike protein including a D614G amino acid substitution. In other examples, the additional antigen binding domain specifically binds to a coronavirus spike protein from coronavirus lineage B.1.617.2, AY.1, AY.2, or AY.3 (e.g., "delta" variant coronaviruses) or a variant thereof. In other examples, the additional antigen binding domain specifically binds to a coronavirus envelope protein or a variant thereof or a coronavirus membrane protein or a variant thereof. In some embodiments, one or more of the additional antigen binding domains specifically binds to a SARS-CoV-2 protein (such as a spike, envelope, or membrane protein). Any combination of additional antigen binding domains can be included in the CAR, such as one or more antigen binding domains that specifically bind a coronavirus spike protein, one or more antigen binding domains that specifically bind a coronavirus envelope protein, one or more antigen binding domains that specifically bind a coronavirus membrane protein, or any combination thereof. In one non-limiting example, the CAR includes CR3022 antigen binding domain disclosed herein and a second antigen binding domain that specifically binds to a coronavirus spike protein and is different from the CR3022 antigen binding domain.

In additional embodiments, the CAR further includes an inducible gene that can be used to eliminate CAR expressing cells (e.g., a "suicide" gene). The inducible gene can be activated in the event of off target side effects, such as cytokine release syndrome ("cytokine storm"). In some examples, expression of the suicide gene is inducible by a small molecule, such as tetracycline or doxycycline (a "TET ON" system) or rapamycin. See, e.g., Gargett et al., *Front. Pharmacol.* 5:235, 2014; Stavrou et al., *Mol. Ther.* 6:1266-1276, 2018. In other examples, the suicide gene is inducible by a Fas domain inducible system. In some examples, the inducible suicide domain is located N-terminal or C-terminal to the antigen binding domain of the CAR, while in other examples, the inducible suicide domain is located C-terminal to the CD3ζ domain of the CAR. The inducible suicide domain is separated from the CAR by a self-cleaving peptides (such as a P2A peptide or T2A peptide).

In other embodiments, the disclosed CARs further include a domain that increases survival or persistence of a modified immune cell expressing the CAR. In some examples, the domain is an intracellular domain from a cytokine receptor, for example, an intracellular domain from interleukin (IL) receptor 15, IL-12 receptor, or IL-18 receptor. In other examples, the domain is an intracellular domain a growth factor receptor, such as an intracellular domain from CD40, NKG2D, NKP40, or NKP46. In some examples, the domain is located C-terminal to the CD3ζ domain of the CAR.

Also provided are nucleic acids encoding the CR3022 scFv and CR3022-CARs disclosed herein. In some embodiments, the antigen binding domain is encoded by a nucleic acid sequence including variable heavy chain (VH) domain complementarity determining region 1 (CDR1), CDR2 and CDR3 nucleic acid sequences of nucleotide positions 91-105, 148-198, and 295-324 of SEQ ID NO: 2, respectively, and variable light chain (VL) domain CDR1, CDR2 and CDR3 nucleic acid sequences of nucleotide positions 481-531, 577-597, and 694-720 of SEQ ID NO: 2, respectively. In some examples, the CR3022 scFv is encoded by a nucleic acid sequence with at least 90% sequence identity (for example, at least 91%, at least 92%, at least 93%, at least 94%, at least 95%, at least 96%, at least 97%, at least 98%, or at least 99% sequence identity) to SEQ ID NO: 2 or includes or consists of the nucleic acid sequence of SEQ ID NO: 2. In other examples, the CR3022-CAR is encoded by a nucleic acid sequence with at least 90% sequence identity (for example, at least 91%, at least 92%, at least 93%, at least 94%, at least 95%, at least 96%, at least 97%, at least 98%, or at least 99% sequence identity) to SEQ ID NO: 4 or includes or consists of the nucleic acid sequence of SEQ ID NO: 4. In other examples, the CR3022-CAR is encoded by a nucleic acid sequence with at least 90% sequence identity (for example, at least 91%, at least 92%, at least 93%, at least 94%, at least 95%, at least 96%, at least 97%, at least 98%, or at least 99% sequence identity) to nucleotides 64-2223 of SEQ ID NO: 4 or includes or consists of the nucleic acid sequence of nucleotides 64-2223 of SEQ ID NO: 4.

The disclosed nucleic acids include DNA, cDNA and RNA sequences which encode the CAR, for example, including the nucleic acid sequences disclosed herein. The coding sequence includes variants that result from the degeneracy (e.g., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see e.g., Stryer, 1988, *Biochemistry*, 3rd Edition, W.H. 5 Freeman and Co., NY).

In addition, the disclosed nucleic acids may be codon-optimized for expression in a given organism. Codon usage bias, the use of synonymous codons at unequal frequencies, is ubiquitous among genetic systems (Ikemura, *J. Mol. Biol.* 146:1-21, 1981; Ikemura, *J. Mol. Biol.* 158:573-97, 1982). The strength and direction of codon usage bias is related to genomic G+C content and the relative abundance of different isoaccepting tRNAs (Akashi, *Curr. Opin. Genet. Dev.* 11:660-666, 2001; Duret, *Curr. Opin. Genet. Dev.* 12:640-9, 2002; Osawa et al., *Microbiol. Rev.* 56:229-264, 1992). Codon usage can affect the efficiency of gene expression. Codon-optimization refers to replacement of at least one codon (such as at least 5 codons, at least 10 codons, at least 25 codons, at least 50 codons, at least 75 codons, at least 100 codons or more) in a nucleic acid sequence with a synonymous codon (one that codes for the same amino acid) more frequently used (preferred) in the organism. Each organism has a particular codon usage bias for each amino acid, which can be determined from publicly available codon usage tables (for example see Nakamura et al., *Nucleic Acids Res.* 28:292, 2000 and references cited therein). For example, a codon usage database is available on the World Wide Web at kazusa.or.jp/codon. One of skill in the art can modify a nucleic acid encoding a particular amino acid sequence, such that it encodes the same amino acid sequence, while being optimized for expression in a particular cell type.

Also provided are functional variants of the CARs or the domains thereof described herein, which retain the biological activity of the CAR of which it is a variant or retains the biological activity of the particular domain. The functional variant can be at least about 80%, about 85%, about 90%, about 91%, about 92%, about 93%, about 94%, about 95%, about 96%), about 97%, about 98%, about 99% or more identical in amino acid sequence to the parent CAR or domain. Substitutions can be made, for example, in one or more of the antigen binding domain, hinge domain, transmembrane domain, and intracellular domains.

In some examples, the functional variant includes the amino acid sequence of the parent CAR or domain with at least one conservative amino acid substitution (such as up to 10 conservative amino acid substitutions, for example, 1, 2, 3, 4, 5, 6, 7, 8, 9, or 10 conservative substitutions). In other examples, the functional variant includes the amino acid sequence of the parent CAR or domain with at least one non-conservative amino acid substitution (such as up to 10 non-conservative amino acid substitutions, for example, 1, 2, 3, 4, 5, 6, 7, 8, 9, or 10 non-conservative substitutions). In this case, the non-conservative amino acid substitution does not interfere with or inhibit the biological activity of the functional variant. The non-conservative amino acid substitution may enhance the biological activity of the functional variant, such that the biological activity of the functional variant is increased as compared to the parent CAR or domain.

The CARs or domains thereof can in some examples, include one or more synthetic amino acids in place of one or more naturally-occurring amino acids. Such synthetic amino acids include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, 2-amino-2-norbornanecarboxylic acid, γ-diaminobutyric acid, α,β-diaminopropionic acid, homophenylalanine, and α-tert-butylglycine. The CARs may be glycosylated, amidated, carboxylated, phosphorylated, esterified, N-acylated, cyclized via, e.g., a disulfide bridge, or converted into an acid addition salt and/or optionally dimerized or polymerized, or conjugated.

In some embodiments, a nucleic acid molecule encoding a disclosed CAR is included in an vector (such as a viral vector) for expression in a host cell, such as an immune cell (for example, an NK cell). In some examples, the expression vector includes a promoter operably linked to the nucleic acid molecule encoding the CAR. Additional expression control sequences, such as one or more enhancers, transcription and/or translation terminators, and initiation sequences can also be included in the expression vector. In some embodiments, a nucleic acid encoding a CAR provided herein is included in a viral vector. Examples of suitable virus vectors include retrovirus (e.g., MoMLV or lentivirus), adenovirus, adeno-associated virus, vaccinia virus, and fowlpox vectors. In specific examples, the CAR-encoding nucleic acid is included in a MoMLV vector, such as an SFG retroviral vector or a pHAGE-CPPT lentiviral vector. In other examples, the vector may be a DNA vector.

In some examples, the vector further includes a nucleic acid sequence encoding at least one additional CAR. In some examples, the additional CAR is specific to a coronavirus antigen, for example, a coronavirus spike protein. In some examples, the one or more additional CARs are included in the vector with a CAR disclosed herein, for example, separated by a self-cleaving peptide, such as a P2A peptide sequence.

III. Cells Expressing CR3022-CARs

Also provided herein are cells (for example, immune cells) that express the disclosed CR3022-CARs. In some embodiments, the immune cells are T cells, NK cells, NKT cells, or macrophages. In particular embodiments, the cells include NK cells.

In some examples, the immune cells (for example, T cells, NK cells, NKT cells, or macrophages) are transduced or transfected with one or more expression vectors including one or more nucleic acids encoding a disclosed CAR. In other examples, the vector (or a DNA encoding the construct) may be introduced by contacting the cells with a nanoparticle including the vector or DNA. In some examples, the cells are irradiated following transduction or transfection (e.g., treated with γ-irradiation, such as at a dose of at least 1,000, at least 2,000, at least 3,000, at least 5,000, at least 7,000, at least 8,000, at least 9,000, at least 10,000, at least 11,000, at least 12,000, or at least 15,000 or about 1,000-15,000, 2,000-12,000, 1,000-5,000, 5,000-10,000, or 8,000-12,000, or about 10,000 Rad), for example, prior to administering to a subject.

In some examples, the transduced or transfected immune cells are isolated T cells, NK cells, NKT cells, or macrophages (such as primary cells or cells obtained from a subject). In one examples, the transduced or transfected cells are isolated NK cells (such as a primary NK cell or NK cells obtained from a subject). In some examples, the immune cells are obtained from peripheral blood, umbilical cord blood, lymph node tissue, or bone marrow. In some examples, the immune cells are also enriched, purified, and/or expanded from a sample from a subject, for example before and/or after transduction with one or more of the disclosed expression vectors. In one example, the transduced or transfected NK cells are an NK cell line.

In one non-limiting embodiment, the cell is an NK-92 cell. NK-92 cells are a NK cell line derived from a patient with non-Hodgkin's lymphoma (e.g., ATCC® CRL-2407™). This cell line has properties of activated NK cells (see, e.g., Gong et al., *Leukemia* 8:652-658, 1994). In another embodiment, the cell is an NK-92MI cell (e.g., ATCC® CRL-2408™). The NK-92MI cell line is an interleukin-2 (IL-2) independent NK cell line, derived from NK-92, which stably expresses human IL-2 (see, e.g., Tam et al., *Hum. Gene Ther.* 10:1359-1373, 1999). NK-92 or NK-92MI cells expressing a CAR (such as a CAR and/or other nucleic acids disclosed herein) can be used herein as an "off the shelf" immunotherapy, since autologous NK cells do not have to be produced for each subject. Other NK cell lines that can be used with the disclosed CARs (or other nucleic acids) described herein include NKL, KHYG-1, and YTS cells.

NK-92-mediated immunotherapy is now undergoing phase I/II clinical trials (Arai et al., *Cytotherapy* 10:625-632, 2008; Tonn et al., *Cytotherapy* 15:1563-1570, 2013). Commonly, NK-92 cells must be irradiated prior to infusion to prevent permanent engraftment. The amount of irradiation required is around 10 Gy. The dose of irradiated NK-92 infusion can be up to $10^{10}$ NK92 cells/m². Importantly, irradiated NK-92 cells have been shown to be safe for infusion in patients, as demonstrated by several NK-92 clinical trials (NCT00900809, NCT00990717, NCT00995137, and NCT01974479).

In some non-limiting embodiments, immune cells are transduced with a vector encoding a CR3022-CAR disclosed herein (e.g., SEQ ID NO: 3). Following transduction, cells expressing the CR3022-CAR can be detected and/or enriched, for example, by flow cytometry. In some examples, the transduced cells (such as NK cells or T cells) are expanded, for example, by cell culture for a period of time following transduction. In some examples, some or all of the modified cells are cryopreserved for later use.

IV. Methods of Treating or Inhibiting Coronavirus

Provided are methods of treating or inhibiting coronavirus infection (such as SARS-CoV1 or SARS-CoV2 infection) in a subject using a CR3022-CAR disclosed herein. In some embodiments, the methods include administering to the subject a composition including a modified immune cell (such as a modified NK cell) expressing a CR3022-CAR (for example, transduced with a vector encoding the CAR) and a pharmaceutically acceptable carrier. In other examples, the methods include administering to the subject a pharmaceutical composition including an expression vector encoding a CR3022-CAR and a pharmaceutically acceptable carrier.

The modified immune cells (such as modified T cells or NK cells) expressing a CR3022-CAR described herein can be incorporated into pharmaceutical compositions. Such compositions typically include a population of cells (for example, a population of CR3022-CAR-NK cells) and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (see, e.g., *Remington: The Science and Practice of Pharmacy*, $22^{nd}$ ed., London, UK: Pharmaceutical Press (2013)). Examples of such carriers or diluents include, but are not limited to, water, saline, Ringer's solutions, dextrose solution, balanced salt solutions, and 5% human serum albumin. Liposomes and non-aqueous vehicles such as fixed oils may also be used. Supplementary active compounds can also be incorporated into the compositions. Actual methods for preparing administrable compositions include those provided in *Remington: The Science and Practice of Pharmacy*, $22^{nd}$ ed., London, UK: Pharmaceutical Press (2013).

In some examples, the subject being treated is infected with or is suspected to be infected with a coronavirus (such as SARS-CoV-1 or SARS-CoV2). In particular examples, the subject has COVID-19 disease, caused by infection with SARS-CoV2. The population of modified immune cells (such as modified T cells or NK cells) is typically administered parenterally, for example intravenously; however, other routes of administration can be utilized. Appropriate routes of administration can be determined based on factors such as the subject, the condition being treated, and other factors.

In some examples, the composition includes about $10^4$ to $10^{12}$ modified immune cells (for example, about $10^4$-$10^8$ cells, about $10^6$-$10^8$ cells, or about $10^6$-$10^{12}$ cells). For example, the composition may be prepared such that about $10^4$ to $10^{10}$ modified cells/kg (such as about $10^4$, $10^5$, $10^6$, $10^7$, or $10^8$ cells/kg) are administered to a subject. In specific examples, the composition includes at least $10^4$, $10^5$, $10^6$, or $10^7$ CR3022-CAR cells (such as CR3022-CAR-NK cells). Multiple doses of the population of modified cells can be administered to a subject. For example, CR3022-CAR cells can be administered daily, every other day, twice per week, weekly, every other week, every three weeks, monthly, or less frequently. A skilled clinician can select an administration schedule based on the subject, the condition being treated, the previous treatment history, and other factors.

In additional examples, the subject is also administered at least one, at least one, at least two, at least three, or at least four cytokine(s) (such as IL-2, IL-15, IL-21, and/or IL-12) to support survival and/or growth of the modified immune cells. In specific, non-limiting examples, at least one cytokine includes IL-2 and IL-15. The cytokine(s) are administered before, after, or substantially simultaneously with the modified cells. In specific examples, at least one cytokine (e.g., IL-2) is administered simultaneously with the CR3022-CAR cells, for example, with CR3022-CAR-NK cells.

EXAMPLES

The following examples are provided to illustrate certain particular features and/or embodiments. These examples

Example 1

Materials and Methods

Antibodies and Reagents

PE anti-human CD3 antibody (clone OKT3), FITC and PE/Cy7 anti-human CD56 antibody (clone HCD56, BioLegend), PE anti-human CD69 antibody (clone FN50, BioLegend), PE anti-human CD8a antibody (clone RPA-T8, BioLegend), APC/Fire 750 anti-human CD226 antibody (DNAM-1) (clone 11A8, BioLegend), APC/Fire 750 anti-human KLRG1 (MAFA) antibody (clone SA231A2, BioLegend), BV421 anti-human CD335 (NKp46) antibody (clone 9E2, BioLegend), PE/Cy7 anti-human CD244 (2B4) antibody (clone C1.7, BioLegend), PE anti-human CD152 (CTLA-4) antibody (clone BNI3), APC anti-human CD366 (Tim-3) antibody (clone F38-2E2), PerCP/Cy5.5 anti-human TIGIT (VSTM3) antibody (clone A15153G), FITC anti-human CD223 (LAG-3) antibody (clone 11C3C65, BioLegend), BV510 anti-human CD314 (NKG2D) antibody (clone 1D11), and APC anti-human CD94 (clone DX22, BioLegend) were purchased from BioLegend (San Diego, CA, USA). APC anti-human CD16 antibody (clone 3G8, BD Biosciences), BV711 anti-human CD314 (NKG2D) antibody (clone 1D11, BD Biosciences), and FITC anti-human CD107a antibody (clone H4A3, BD Biosciences) were purchased from BD Biosciences (San Jose, CA, USA). PE anti-human NKG2C/CD159c antibody (clone 134591, R&D Systems) were purchased from R&D Systems. AF647 Goat anti-human IgG(H+L) F(ab')$_2$ fragment antibody was purchased from Jackson ImmunoResearch (West Grove, PA, USA). Anti-SARS-CoV-2 Coronavirus Spike protein (subunit 1) polyclonal antibody was purchased from Invitrogen (Carlsbad, CA, USA). Anti-SARS-CoV-2 Spike RBD rabbit polyclonal antibody was purchased from SinoBiological (Beijing, China). Anti-His mouse monoclonal antibody IgG1 (clone H-3) was purchased from Santa Cruz Biotechnology (Dallas, TX, USA). Alexa Fluor 488 goat anti-rabbit IgG (H+L) and Alexa Fluor 488 goat anti-mouse IgG1 (γ1) were purchased from Fisher Scientific (Waltham, MA).

Cell Lines 293T cell line was purchased from the American Type Culture Collection (ATCC). 293T-hACE2 cell line is a gift from Dr. Abraham Pinter (Rutgers-New Jersey Medical School, PHRI). To maintain the stable expression of hACE2, 293T-hACE2 cells were cultured in DMEM (Corning) supplemented with 10% (v/v) fetal bovine serum (FBS), 100 U/mL Penicillin-Streptomycin (Corning), and 1 µg/mL of puromycin at 37° C. under 5% (v/v) $CO_2$. To establish transient 293T-hACE2-RBD, 293T-hACE2 cells were transfected with 0.5 µg of SARS-CoV-2-RBD plasmid (a gift from Dr. Abraham Pinter) per well in a 24-well plate (Eppendorf) for 48 hours at 37° C. under 5% (v/v) $CO_2$. Similarly, 293T-hACE2-FFLuc-GFP-RBD cells were transfected with 0.25 µg of SARS-CoV-2-RBD plasmid and 0.25 µg of pHAGE-FFLuc-GFP per well in a 24-well plate (Eppendorf) for 48 hours at 37° C. under 5% (v/v) $CO_2$. Cells were harvested and immediately used for CD107a degranulation, $^{51}$Cr release, and FFLuc reporter assays.

CR3022-CAR Construction and Retrovirus Production

A codon-optimized DNA fragment was synthesized by GENEWIZ encoding the CR3022-specific scFv and subcloned into the SFG retroviral vector retroviral backbone in-frame with the hinge component of human IgG1, CD28 trans-membrane domain, intracellular domain CD28 and 4-1BB, and the ζ chain of the human TCR/CD3 complex. To produce CR3022-CAR retrovirus, 293T cells were transfected with CR3022-CAR in SFG backbone, RDF, and PegPam3. CR3022-CAR retrovirus was harvested after 48-72 hours and transduced to NK92MI cells in a 24-well plate coated with 0.5 µg/ml of RetroNectin diluted in PBS (Clontech). Two days later, cells were transferred to 75 cm$^2$ flask (Corning) and maintained in 35 ml complete NK92MI medium (MEM-α with 12.5% (v/v) FBS, 12.5% (v/v) heat inactivated horse serum, 11 µM βME, 2 µM folic acid, and 20 µM inositol) supplemented with 200 U/mL IL-2 (PeproTech). To determine the expression of CAR, cells were stained for CD56 and anti-human IgG(H+L) F(ab')$_2$ fragment and analyzed by flow cytometry.

CR3022-CAR and RBD Binding Assay

To evaluate the binding activity of CR3022-CAR to RBD domain of SARS-CoV-2-S, CR3022-CAR and NK92MI (5×10$^5$) cells were incubated with 5 µg of His-gp70-RBD recombinant protein (a gift from Dr. Abraham Pinter) in DPBS buffer (0.5 mM $MgCl_2$ and 0.9 mM $CaCl_2$ in PBS) for 30 minutes on ice. Cells were washed twice with PBS, stained with anti-His in FACS buffer (0.2% FBS in PBS) for 30 minutes on ice and washed twice with PBS. Cells were then stained with anti-mouse (IgG1) secondary antibody in FACS buffer for 30 minutes on ice, washed twice with PBS, and analyzed by Flow Cytometry.

CR3022-CAR and Pseudotyped SARS-CoV-2-S Viral Particles Binding Assay

CR3022-CAR, NK92MI, and 293T-hACE2 (5×10$^5$) cells were first equilibrated with BM (complete RPMI-1640 containing 0.2% BSA and 10 mM HEPES pH 7.4). Due to the non-specific binding to the CR3022-CAR of the secondary antibody, cells were first blocked with anti-human IgG(H+L) F(ab')$_2$ fragment for 30 minutes on ice in BM and washed thrice with PBS. Pseudotyped SARS-CoV-2-S (Genscript), full-length recombinant S protein (Acrobio systems), and S1 subunit recombinant protein (a gift from Dr. Abraham Pinter) were diluted with BM to appropriate concentrations. 4×10$^6$IFU of pseudotyped SARS-CoV-2-S, or 2 µg of full-length recombinant S protein, or 2 µg of S1 subunit recombinant protein was added to designated wells of a 96-well V bottom plate. Plate was spun at 600×g for 30 minutes at 32° C., then was incubated at 37° C. under 5% (v/v) $CO_2$ for 1 hour. Cells were washed twice with PBS, stained with anti-S1 in FACS buffer (0.2% FBS in PBS) for 30 minutes on ice and washed thrice with PBS. Cells were then stained with goat anti-rabbit secondary antibody in FACS buffer for 30 minutes on ice, washed thrice with PBS, and analyzed by Flow Cytometry.

Flow Cytometry Analysis

NK92MI and CR3022-CAR cells were stained and washed as previously described. Cells were analyzed on a FACS LSRII or an LSR Fortessa flow cytometer (BD). PMT voltages were adjusted and compensation values were calculated before data collection. Data were acquired using FACS Diva software (BD) and analyzed using FlowJo software (BD).

CD107a Degranulation Assay

Expanded NK cells (5×10$^4$) were incubated with 1×10$^5$ 293 T cells in V-bottomed 96-well plates in complete RPMI-1640 media at 37° C. for 2 hours. The cells were harvested, washed, and stained for CD3, CD56, and CD107a with GolgiStop (BD Biosciences) for 30 minutes, and analyzed by flow cytometry.

$^{51}$Cr Release Assay

To evaluate the cytotoxic activity of CAR-NK cell, the standard 4-hour $^{51}$Cr release assay was used. Briefly target cells were labeled with $^{51}$Cr at 37° C. for 2 hours and then resuspended at $1\times10^5$/mL in NK-92MI culture medium with 10% FBS without IL-2. Then, $1\times10^4$ target cells were incubated with serially diluted CAR-NK or NK-92MI cells at 37° C. for 4 hours. After centrifugation, the supernatants were collected and the released $^{51}$Cr was measured with a gamma counter (Wallac, Turku, Finland). The cytotoxicity (as a percentage) was calculated as follows:

[(sample−spontaneous release)/(maximum release−spontaneous release)]×100.

FFLuc Reporter Assay

To quantify the cytotoxicity of CAR-modified immune cells, we also developed the FFLuc reporter system assay. Briefly, an optical 96-well plate (Greiner Bio-One™ No: 655098) was precoated with Retronectin (0.5 µg/ml in PBS) and placed at 4° C. overnight. Then, the following day, the wells were aspirated and 293T-hACE2-FFLuc-GFP-RBD and 293T-hACE2 cells were pre-seeded at $1\times10^4$ target cells/well in 100 µL/well of DMEM supplemented with 10% FBS. The plate was centrifuged for 5 minutes at 350×g. In a separate 96-well plate, CR3022-CAR-NK-92MI and NK-92MI cells were resuspended at a concentration of $1\times10^6$ cells/ml. Serial dilutions of effector cells were then prepared according to the effector/target ratio using NK-92MI medium. Then, the effector cells were added to each well of the optical plate (100 µL/well) and incubated at 37° C. under 5% (v/v) $CO_2$ for 4 hours and then the supernatant was gently discarded. 100 µL of working concentration D-Luciferin was added to each well with the lights turned off. A microplate reader (BioTek, USA) was used to quantify the data. The data were quantified by converting the obtained values to percentage of specific lysis by the following equation:

Specific Lysis Percentage (%)=[1−(S−E)/(T−M)]×100 where S is the value of luminescence of the sample well, E is the value of luminescence of the "effector cell only" well compared to the sample well, T is the mean value of luminescence of "Target cell only" wells, and M is the mean value of luminescence of "blank medium only" wells.

Statistical Analysis

Data were represented as means±SEM. The statistical significance was determined using a two-tailed unpaired Student t test, a two-tailed paired Student t test, a two-way ANOVA, where indicated. P<0.05 was considered statistically significant.

Example 2

Generation and Testing of CR3022-CAR-NK Cells

Generation of CR3022-CAR-NK-92MI Cells

To develop an NK cell-based immunotherapy to treat COVID-19 patients, we modified NK cells with a CAR molecule specific against SARS-CoV-2 S protein. Previous studies showed that the genome sequence of SARS-CoV-2 is highly similar to that of SARS-CoV-1 (Zhou et al., *Nature* 579:270-273, 2020). Recent studies also demonstrated that a previously isolated neutralizing antibody from a convalescent SARS patient (and later named CR3022) can specifically bind to the RBD of SARS-CoV-2 spike protein (Tian et al., *Emerg. Microbes Infect.* 9:382-385, 2020). Thus, we cloned the scFv domain of CR3022 into an SFG retroviral vector that contains a human IgG1 hinge and CH2-CH3 domain, CD28 transmembrane (TM) domain and intracellular domain, 4-1BB-Ligand intracellular domain, and CD3zeta intracellular domain (FIG. 1A). Specifically, the scFv domain of CR3022 antibody was chosen because of its strong binding activity against both SARS-CoV-1 and SARS-CoV-2 S proteins.

Figure 1B:
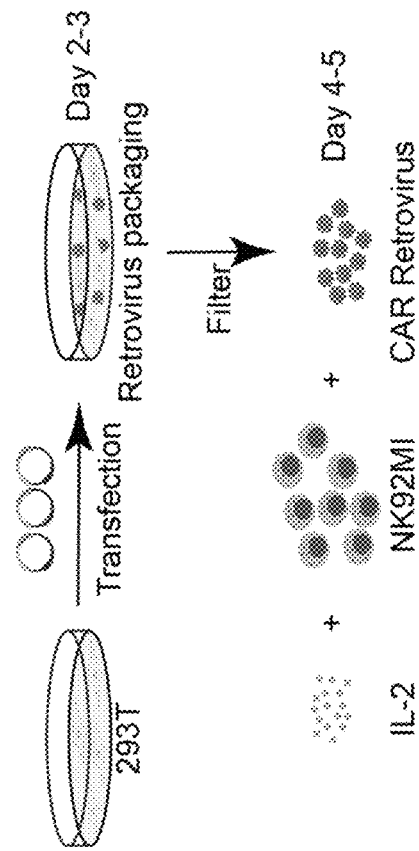
Figure 1C:
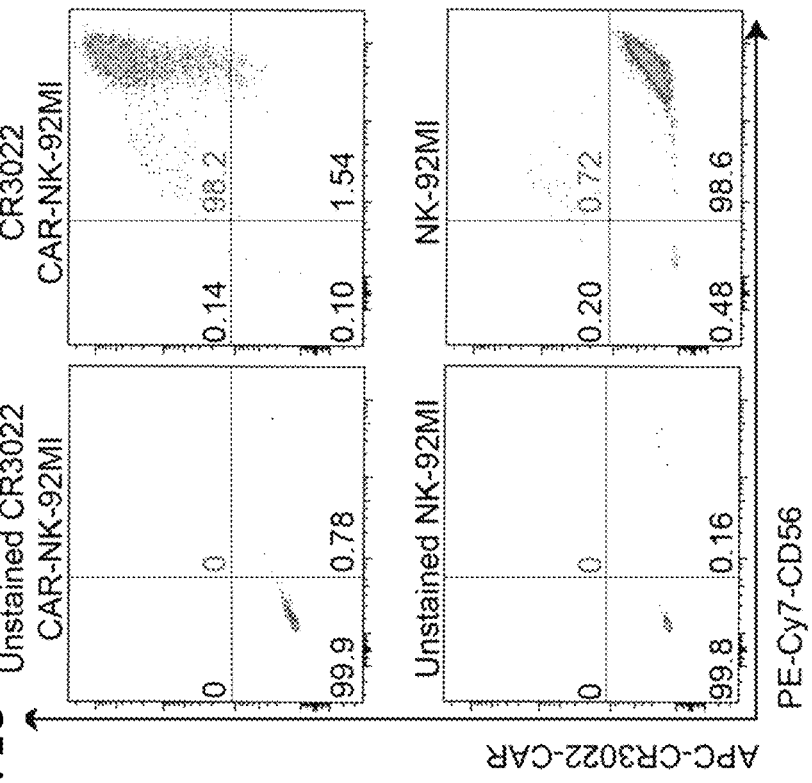

CR3022-CAR-NK cells were successfully generated in the human NK-92 cell line background (FIG. 1A). Specifically, the NK-92 cell line was transduced with CR3022-CAR. Then, the subsequent CR3022-CAR positive NK-92 cells were sorted by flow cytometry. Sorted CR3022-CAR-NK-92MI cells were maintained for 2 months to verify CAR expression (data not shown). The generation of CR3022-CAR-NK cell is schematically shown in FIG. 1B. 293T cells were transfected with a combination of plasmids containing CR3022-CAR in the SFG backbone, RDF, and PegPam3. The SFG retrovirus particles were used to transduce NK-92MI cells. After 4-5 days, NK-92MI and CR3022-CAR cells were stained with CD56 and human IgG (H+L) and the CAR expression was analyzed by flow cytometry (FIG. 1C). Greater than 98% of CD56$^+$ CR3022-CAR$^+$ NK-92MI cells were observed (FIG. 1C). This establishes the stable membrane expression of CR3022-CAR-NK cells.

Characteristics of CR3022-CAR-NK92MI Cells

Figure 2A:
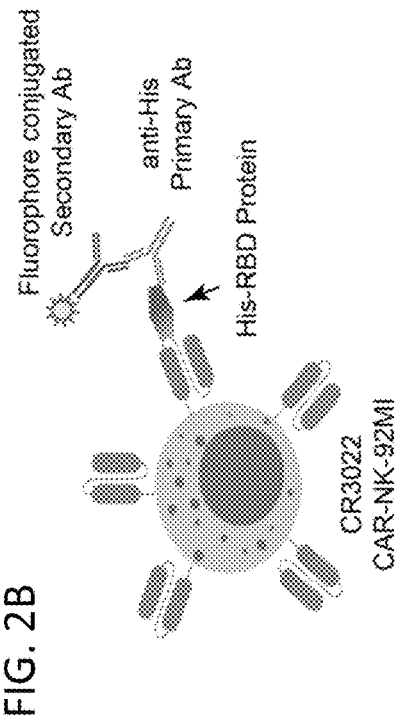
FIGS. 2A-2C show that CR3022-CAR-NK92MI cells bind to RBD domain of SARS-CoV-2-S protein.

To have a better understanding of the immunophenotype of CR3022-CAR-NK-92MI, the expression of several key immunoreceptors on CR3022-CAR-NK-92MI cells were examined by flow cytometry. These receptors include TIGIT, LAG-3, TIM-3, KLRG1, CTLA-4, PD-1, CD69, CD8A, NKG2C, CD94, DNAM-1, 2B4, NKG2D, NKP46, and CD16 (FIG. 2A). The expression of these activating and inhibitory receptors were comparable between parental NK-92MI and CR3022-CAR-NK-92MI cells. Surprisingly, the expressions of CD94 and 2B4 receptors significantly decreased in CR3022-CAR-NK-92MI cells. Overall, these key activating and inhibitory receptors between parental NK-92MI and CR3022-CAR-NK-92MI cells were similar, indicating the stable characteristics of NK-92MI at pre- and post-transduction stages.

Figure 2B:
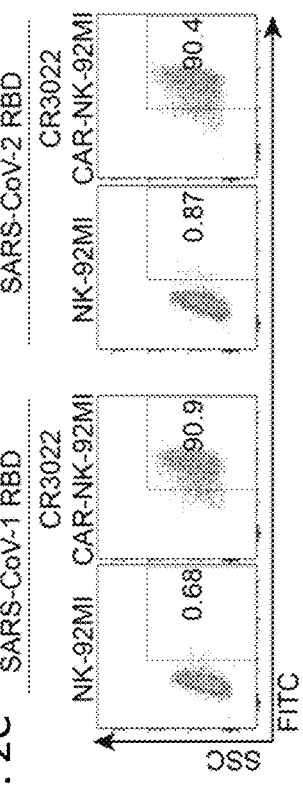
Figure 2C:
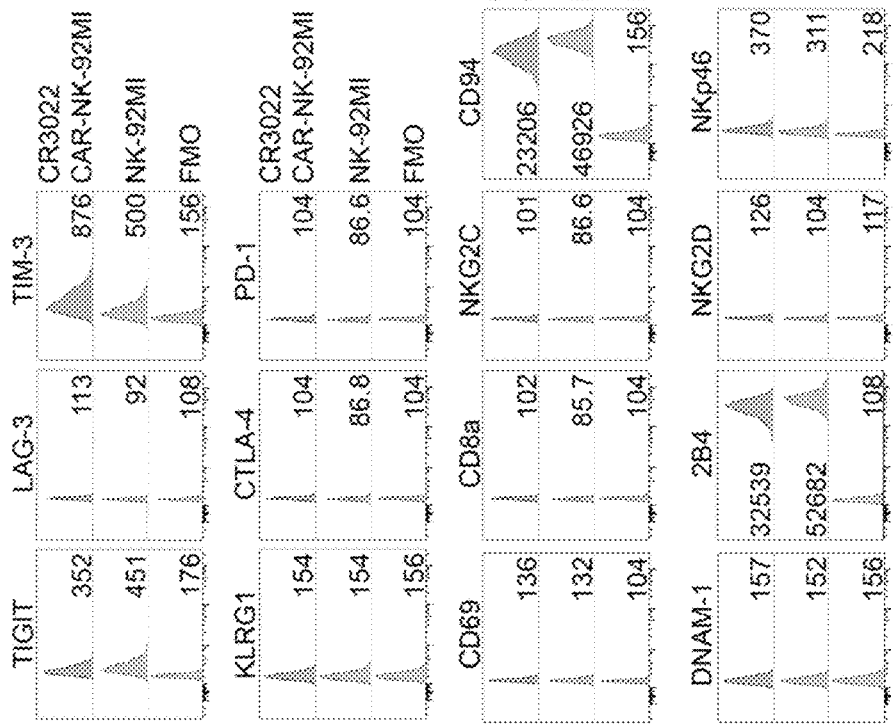

After successful establishment of CR3022-CAR-NK-92MI cells, the binding activity of CR3022-CAR cells to the RBD domain of SARS-CoV-2-S protein was assessed. CR3022-CAR-NK-92MI cells and NK-92MI cells were incubated with the recombinant His-RBD protein from SARS-CoV-1 or SARS-CoV-2, respectively. The complex of CR3022-CAR-NK-92MI and the His-RBD protein was then recognized by anti-His and its corresponding secondary antibody conjugated with a fluorophore (FIG. 2B). Flow cytometry was used to evaluate the binding efficiency of CR3022-CAR to the RBD of S protein from either SARS-CoV-1 or SARS-CoV-2. Consistent with earlier results from previous studies (Tian et al., *Emerg. Microbes Infect.* 9:382-385, 2020), CR3022 bound to the RBD of both SARS-CoV-1 and SARS-CoV-2 (FIG. 2C). Therefore, CR3022-CAR-NK-92MI cells can specifically bind to the recombinant His-RBD protein from SARS-CoV-1 and SARS-CoV-2.

CR3022-CAR-NK Cells Bind to Pseudotyped SARS-CoV-2-S Viral Particles

The partial RBD domain of SARS-CoV-2-S may not fully reflect the complexity of SARS-CoV-2 viral particles. Therefore, the binding activity of CR3022-CAR cells to pseudotyped SARS-CoV-2-S viral particles purchased from GenScript, USA was evaluated. Similar to the concept in FIG. 2B, CR3022-CAR-NK-92MI bound to the pseudotyped SARS-CoV-2-S viral particles. The CR3022-CAR- NK-92MI and SARS-CoV-2-S viral particle complex can be recognized by the binding of anti-spike antibody and its corresponding fluorophore-conjugated secondary antibody (FIG. 3A). Previous studies showed that the RBD of spike protein binds to ACE2 and facilitates SARS-CoV-2 entry (Lan et al., Nature 581:215-220, 2020). As a positive control, 293T-hACE2 was included in the experiment (FIG. 3B). In addition, spike recombinant proteins, full-length and S1 subunit containing RBD were included as an additional control group. As expected, CR3022-CAR-NK-92MI cells were able to bind to the pseudotyped SARS-CoV-2-S viral particles (FIG. 3C). However, the binding efficiency was slightly lower than that of full-length spike recombinant protein and S1 subunit containing RBD protein groups (FIG. 3C). Surprisingly, 293T-hACE2 cells showed a weaker binding efficiency with the pseudotyped SARS-CoV-2 viral particles, compared to that of CR3022-CAR-NK-92MI cells, indicating that the binding activities of CR3022-CAR-NK-92MI was superior to the natural receptor of SARS-CoV-2 virus.

CR3022-CAR-NK Cells can be Activated by SARS-CoV-2 Spike Protein Receptor Binding Domain Expressing Infected Target Cells and Specifically Kill their Susceptible Target Cells After successful establishment of CR3022-CAR-NK cells and demonstration of recombinant His-RBD protein and pseudotyped SARS-CoV-2-S viral particle binding, CR3022-CAR-NK cells activation by SARS-CoV-2-S infected target cells was evaluated. To test this, the receptor binding domain (RBD) of SARS-CoV-2 spike protein was transfected into 293T-hACE2 cells (commonly used cell line for studying the SARS-CoV-2 virus) by transfecting these two cells with an RBD encoding plasmid (FIG. 4A and FIG. 5). Greater than 90% of transfection efficiencies on 293T-hACE2 cell were obtained. The expression of RBD proteins on 293T-hACE2 cells were verified by flow cytometry (FIG. 4B and FIG. 5). After successful establishment of these 293T-hACE2-RBD target cells, activation CR3022-CAR-NK-92MI cells by these target cells was evaluated using the conventional CD107a assay. The surface level expression of CD107a molecules on CR3022-CAR-NK-92MI cells after co-culturing with these 293T-hACE2-RBD target cells were significantly increased, which was measured by both the percentage and mean fluorescence intensity (MFI) of CD107a on CR3022-CAR-NK92-MI cells, compared to cells cocultured with the parent cells alone (FIG. 4C). In addition, the production of TNF-alpha and perforin were greatly increased on CR3022-CAR-NK-92MI cells after co-culturing with these 293T-hACE2-RBD target cells (data not shown).

Next, the capacity of CR3022-CAR-NK-92MI cells to eradicate SARS-CoV-2 infected target cells (including 293T-hACE2) was tested. For 293T-hACE2 cells, an additional plasmid encoding firefly luciferase (FFLuc) tagged with green fluorescent protein (GFP) was also transfected to perform the standard Luciferase assay. Successful luciferase expression on 293T-hACE2 cells was confirmed by flow cytometry analysis (FIG. 4B). Compared to control NK-92MI cells, CR3022-CAR-NK-92MI cells showed significantly higher killing capacities against 293T-hACE2 cells transfected with RBD (FIG. 4D).

To directly test whether CR3022-CAR-NK-92MI cells can kill SARS-CoV-2 infected target cells in vitro, the 4-hour Chromium-51 ($^{51}$Cr) release assay (a gold standard assay) was used. The data showed that CR3022-CAR-NK-92MI cells effectively killed 293T-hACE2-RBD cells by in vitro $^{51}$Cr release assay (FIG. 5C). Thus, by using both the luciferase killing assay platform and $^{51}$Cr release assay platforms using two different transfected cell lines, it has been demonstrated that the CR3022-CAR-NK-92MI cells can kill SARS-CoV-2 infected target cells.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

---

We claim:

1. A chimeric antigen receptor comprising at least 90% sequence identity to the amino acid sequence of SEQ ID NO: 3 or at least 90% sequence identity to amino acids 22-740 of SEQ ID NO: 3,
wherein the chimeric antigen receptor comprises an antigen binding domain that specifically binds a coronavirus spike protein, comprising an amino acid sequence comprising variable heavy chain (VH) domain complementarity determining region 1 (CDR1), CDR2 and CDR3 amino acid sequences of amino acid positions 31-35, 50-66, and 99-108 of SEQ ID NO: 1, respectively, and variable light chain (VL) domain CDR1, CDR2 and CDR3 amino acid sequences of amino acid positions 161-177, 193-199, and 232-240 of SEQ ID NO: 1, respectively.

2. The chimeric antigen receptor of claim 1, wherein the antigen binding domain comprises:
a VH domain that comprises the amino acid sequence of SEQ ID NO: 5;
a VL domain that comprises the amino acid sequence of SEQ ID NO: 7; or both.

3. The chimeric antigen receptor of claim 1, wherein the antigen binding domain comprises the amino acid sequence of SEQ ID NO: 1.

4. The chimeric antigen receptor of claim 1 wherein the chimeric antigen receptor comprises the amino acid sequence of SEQ ID NO: 3 or comprises the amino acid sequence of amino acids 22-740 of SEQ ID NO: 3.

5. The chimeric antigen receptor of claim 1, further comprising one or more additional antigen binding domains.

6. The chimeric antigen receptor of claim 5, wherein the one or more additional antigen binding domains specifically binds a coronavirus spike protein, a coronavirus envelope protein, a coronavirus membrane protein, or any combination thereof.

7. The chimeric antigen receptor of claim 6, wherein the antigen binding domains specifically bind a coronavirus spike protein and the antigen binding domains are different.

8. The chimeric antigen receptor of claim 1, further comprising an inducible suicide molecule.

9. The chimeric antigen receptor of claim 8, wherein the suicide molecule comprises caspase 9.

10. A nucleic acid encoding the chimeric antigen receptor of claim 1, wherein the nucleic acid comprises at least 90% sequence identity to the nucleic acid sequence of SEQ ID NO: 4 or at least 90% sequence identity to nucleotides 64-2223 of SEQ ID NO: 4.

11. The nucleic acid of claim 10, wherein the nucleic acid comprises the nucleic acid sequence of SEQ ID NO: 4, or comprises the nucleic acid sequence of nucleotides 64-2223 of SEQ ID NO: 4.

12. A vector comprising the nucleic acid of claim 10.

13. The vector of claim 12, wherein the vector is a viral vector.

14. A modified immune cell expressing the chimeric antigen receptor of claim 1.

15. The modified immune cell of claim 14, wherein the immune cell is a T cell, natural killer (NK) cell, NKT cell, or macrophage.

16. The modified immune cell of claim 15, wherein the immune cell is an NK cell.

17. The modified immune cell of claim 16, wherein the NK cell is an NK-92 cell or NK-92MI cell.

18. A method of treating a subject with a coronavirus infection, comprising administering an effective amount of the modified immune cell of claim 14 to the subject.

19. The method of claim 18, wherein the subject is infected with SARS-COV-1 or SARS-COV-2.

* * * * *